United States Patent [19]

Kadin

[11] Patent Number: 4,721,712

[45] Date of Patent: Jan. 26, 1988

[54] 1,3-DISUBSTITUTED 2-OXINDOLES AS ANALGESIC AND ANTI-INFLAMMATORY AGENTS

[75] Inventor: Saul B. Kadin, New London, Conn.

[73] Assignee: Pfizer Inc., New York, N.Y.

[21] Appl. No.: 670,697

[22] Filed: Nov. 13, 1984

Related U.S. Application Data

[63] Continuation-in-part of Ser. No. 619,861, Jun. 12, 1984, abandoned, which is a continuation-in-part of Ser. No. 577,903, Feb. 7, 1984, abandoned.

[51] Int. Cl.$^4$ .................. A61K 31/495; A61K 31/40; C07D 241/12; C07D 209/34
[52] U.S. Cl. ................................. 514/253; 514/256; 514/333; 514/338; 514/339; 514/361; 514/362; 514/365; 514/372; 514/374; 514/378; 514/411; 514/414; 514/418; 544/333; 544/405; 546/256; 546/270; 546/273; 548/127; 548/134; 548/181; 548/214; 548/236; 548/247; 548/248; 548/431; 548/450; 548/454; 548/465; 548/468; 548/486
[58] Field of Search ............. 514/337, 419, 411, 414, 514/333, 365, 372, 374, 378, 361, 362, 338, 339, 256, 253, 418; 548/486, 450, 431, 454, 468, 181, 214, 236, 247, 248, 127, 134, 465; 546/270, 273, 256; 544/333, 405

[56] References Cited

U.S. PATENT DOCUMENTS

| 3,462,450 | 8/1969 | Shen ............................... 260/326.12 |
| 3,519,592 | 7/1970 | Holden ................................. 260/240 |
| 3,522,272 | 7/1970 | Chemerda et al. ................... 548/468 |
| 3,631,177 | 12/1971 | Holden ................................. 260/325 |
| 3,634,453 | 1/1972 | McManus et al. .................... 260/325 |
| 3,749,731 | 7/1973 | Zinnes et al. ...................... 260/306.8 |
| 3,856,967 | 12/1974 | Allais et al. ........................... 424/274 |
| 3,975,531 | 8/1976 | Welstead et al. ..................... 424/274 |
| 4,012,394 | 3/1977 | Descamps et al. ................... 546/194 |
| 4,658,037 | 4/1987 | Kadin .................................. 548/450 |
| 4,665,194 | 5/1987 | Crawford ............................. 548/486 |

FOREIGN PATENT DOCUMENTS

| 46-14898 | 4/1971 | Japan . |
| 48-14667 | 2/1973 | Japan . |
| 1158532 | 7/1969 | United Kingdom . |
| 1206995 | 9/1970 | United Kingdom . |

OTHER PUBLICATIONS

McOnie, *Protective Groups in Organic Chemistry*, Plenum Press, New York (1923), 54–55.
Ariens, E. J., Drug Design, Academic Press, New York (1971), pp. 10–11.
Wenkert et al., *Journal of the American Chemical Society*, 80, 4899 (1958).
Bunnett et al., *Organic Syntheses*, vol. 40, 1 (1960).
Capuano et al., *Chemische Berichte*, 105, 2539 (1972).
El-Enany et al., Bulletin of the Faculty of Pharmacy (Cairo University), 14, 29 (1975).
Buchel et al., Z. Anal. Chemie, 190, 243 (1962).
Pakula et al., *Chemical Abstracts*, 72:12563(k) (1970).
Brenner et al., *Chemical Abstracts*, 72:12565(n) (1970).
Shen et al., *Chemical Abstracts*, 72:12566(p) (1970).

*Primary Examiner*—Mary E. Ceperley
*Attorney, Agent, or Firm*—Peter C. Richardson; Lawrence C. Akers; J. Trevor Lumb

[57] ABSTRACT

Certain 2-oxindole-1-carboxamide compounds having an acyl substituent at the 3-position, and also on the carboxamide nitrogen atom, are inhibitors of the cyclooxygenase (CO) and lipoxygenase (LO) enzymes, and are useful as analgesic agents and anti-inflammatory agents in mammalian subjects. These 2-oxindole-1-carboxamide compounds are of particular value for acute administration for ameliorating pain in human patients recovering from surgery or trauma, and also for chronic administration to human subjects for alleviating the symptoms of chronic diseases, such as rheumatoid arthritis and osteoarthritis. Certain 2-oxindole-1-carboxamide compounds unsubstituted at C-3, but having an acyl substituent on the carboxamide nitrogen atom, are useful as intermediates to the aforementioned analgesic and anti-inflammatory agents.

45 Claims, No Drawings

1,3-DISUBSTITUTED 2-OXINDOLES AS ANALGESIC AND ANTI-INFLAMMATORY AGENTS

CROSS-REFERENCE TO RELATED APPLICATIONS

This application is a continuation-in-part of application Ser. No. 619,861, filed June 12, 1984, and now abandoned, which is a continuation-in-part of application Ser. No. 577,903, filed Feb. 7, 1984, and now abandoned.

BACKGROUND OF THE INVENTION

This application relates to new chemical compounds which are of value as new medicinal agents. More particularly the new chemical compounds are derivatives of 2-oxindole-1-carboxamide, and they are further substituted at the 3-position and on the carboxamide nitrogen by an acyl group. These new chemical compounds are inhibitors of both the cyclooxygenase (CO) and lipoxygenase (LO) enzymes.

The compounds of this invention possess analgesic activity in mammals, particularly man, and they are useful therefore for acute administration for ameliorating or eliminating pain, such as the pain experienced by patients recovering from surgery or trauma.

In addition to their usefulness for acute administration to combat pain, the compounds of this invention are useful for chronic administration to mammals, particularly man, to alleviate the symptoms of chronic diseases, such as the inflammation and pain associated with rheumatoid arthritis and osteoarthritis.

SUMMARY OF THE INVENTION

This invention provides novel 2-oxindole compounds of the formula

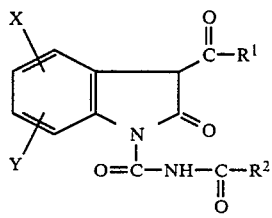

and the pharmaceutically-acceptable base salts thereof; wherein

X is selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons, trifluoromethyl, alkylsulfinyl having 1 to 4 carbons, alkylsulfonyl having 1 to 4 carbons, nitro, phenyl, alkanoyl having 2 to 4 carbons, benzoyl, thenoyl, alkanamido having 2 to 4 carbons, benzamido and N,N-dialkylsulfamoyl having 1 to 3 carbons in each of said alkyls; and Y is selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons and trifluoromethyl;

or X and Y when taken together are a 4,5-, 5,6-or 6,7-methylenedioxy group or a 4,5-, 5,6- or 6,7-ethylenedioxy group;

or X and Y when taken together and when attached to adjacent carbon atoms, form a divalent radical Z, wherein Z is selected from the group consisting of

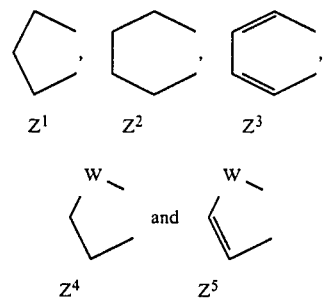

wherein W is oxygen or sulfur;

$R^1$ is selected from the group consisting of alkyl having 1 to 6 carbons, cycloalkyl having 3 to 7 carbons, phenyl, substituted phenyl, phenylalkyl having 1 to 3 carbons in said alkyl, (substituted phenyl)alkyl having 1 to 3 carbons in said alkyl, phenoxyalkyl having 1 to 3 carbons in said alkyl, (substituted phenoxy)alkyl having 1 to 3 carbons in said alkyl, naphthyl and $-(CH_2)_n-Q-R°$;

wherein the substituent on said substituted phenyl, said (substituted phenyl)alkyl and said (substituted phenoxy)alkyl is selected from the group consisting of fluoro, chloro, alkyl having 1 to 3 carbons, alkoxy having 1 to 3 carbons and trifluoromethyl; n is zero, 1 or 2; Q is a divalent radical derived from a compound selected from the group consisting of furan, thiophene, pyrrole, thiazole, isothiazole, oxazole, isoxazole, 1,2,3-thiadiazole, 1,2,5-thiadiazole, tetrahydrofuran, tetrahydrothiophene, pyridine, pyrimidine, pyrazine, benzo[b]furan and benzo[b]thiophene; and R° is hydrogen or alkyl having 1 to 3 carbons;

and $R^2$ is selected from the group consisting of alkyl having 1 to 6 carbons, cycloalkyl having 3 to 7 carbons, phenoxymethyl, furyl, thienyl, pyridyl and

wherein $R^3$ and $R^4$ are each selected from the group consisting of hydrogen, fluoro, chloro, alkyl having 1 to 4 carbons, alkoxy having 1 to 4 carbons and trifluoromethyl.

Said compounds of formula I are active as analgesic agents, and as agents for treating inflammatory diseases, such as the arthritides. Accordingly this invention also provides a method of eliciting an analgesic response in a mammalian subject, especially man; a method of treating an inflammatory disease in a mammalian subject, especially man; and pharmaceutical compositions comprising a compound of formula I and a pharmaceutically-acceptable carrier.

A first preferred group of compounds of this invention consists of the compounds of formula I, wherein X and Y are each hydrogen and $R^1$ is selected from the group consisting of 2-furyl, 2-thienyl and (2-thienyl)methyl. Among this first preferred group, particularly preferred compounds are those wherein $R^2$ is phenyl.

A second preferred group of compounds of this invention consists of the compounds of formula I, wherein X is 5-chloro, Y is hydrogen and $R^1$ is selected from the group consisting of 2-furyl, 2-thienyl and (2-thienyl)methyl. Among this second preferred group, particularly preferred compounds are those wherein $R^2$ is cyclohexyl.

Especially preferred individual compounds of the invention are:

N-benzoyl-3-(2-furoyl)-2-oxindole-1-carboxamide (I:X is hydrogen; Y is hydrogen; $R^1$ is 2-furyl; $R^2$ is phenyl) and N-cyclohexylcarbonyl-5-chloro-3-(2-thenoyl)-2-oxindole-1-carboxamide (I:X is 5-chloro; Y is hydrogen; $R^1$ is 2-thienyl; $R^2$ is cyclohexyl).

Yet further this invention provides novel compounds of the formula

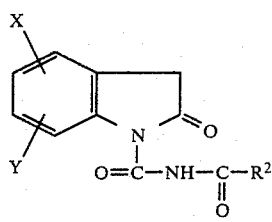

(II)

wherein X, Y and $R^2$ are as defined previously. The compounds of formula II are useful as intermediates to the compounds of formula I.

DETAILED DESCRIPTION OF THE INVENTION

The analgesic and antiinflammatory compounds of this invention are the compounds of formula I, wherein X, Y, $R^1$ and $R^2$ are as defined previously. Thus, the compounds of this invention are derivatives of 2-oxindole, the bicyclic amide of the formula

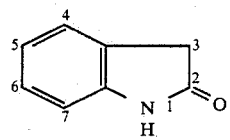

More particularly, the analgesic and antiinflammatory agents of this invention have an N-acylcarboxamido substituent, —C(=O)—NH—C(=O)—$R^2$, at the 1-position and an acyl substituent, —C(=O)—$R^1$, at the 3-position of 2-oxindole, and the benzo ring can be further substituted by X and Y groups. X and Y can be certain monovalent substituents as defined previously, or X and Y when on adjacent carbon atoms on the benzo ring can represent a methylenedioxy group, —OCH$_2$O—, or ethylenedioxy group, —OCH$_2$CH$_2$O—. Yet further, X and Y, when they are attached to adjacent carbon atoms of the benzo ring of the 2-oxindole, can form a divalent unit, Z, such that when Z is taken with the carbon atoms to which it is attached it forms a fused carbocyclic or heterocyclic ring. Certain divalent groups for Z (i.e. $Z^1$-$Z^5$) have been listed earlier. Thus, when Z is $Z^1$, X and Y when taken with the carbons to which they are attached represent a fused cyclopentene ring; and when Z is $Z^5$, X and Y when taken with the carbons to which they are attached represent a fused furan or thiophene ring. Moreover, it is to be understood that when Z is $Z^4$ or $Z^5$, the Z group can be attached in either of two possible ways. Thus, for example, when X and Y are at C-5 and C-6 and they are $Z^5$, the formula I embraces both of the following formulae:

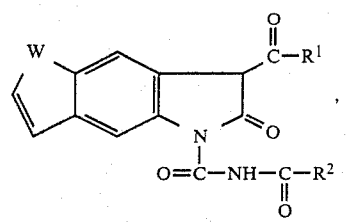

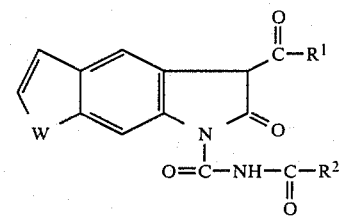

Additionally, as will be appreciated by one skilled in the art, the analgesic and anti-inflammatory compounds of this invention of formula I, wherein X, Y, $R^1$ and $R^2$ are defined previously, are capable of enolization, and therefore they can exist in one or more tautomeric (enolic) forms. All such tautomeric (enolic) forms of the compounds of formula I are considered to be within the scope of this invention.

The compounds of formula I are prepared from the appropriate 2-oxindole compound of the formula

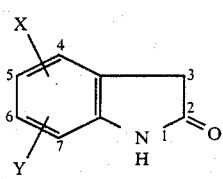

(III)

wherein X and Y are as defined previously. This is accomplished by attaching the substituent —C(=O)—NH—C(=O)—$R^2$ to the 1-position and the substituent —C(=O)—$R^1$ to the 3-position. These substituents can be attached in either order, and this leads to two variations in the method for making the compounds of formula I, as shown in the Scheme.

SCHEME

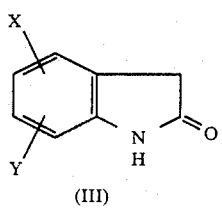

(III)

-continued
SCHEME

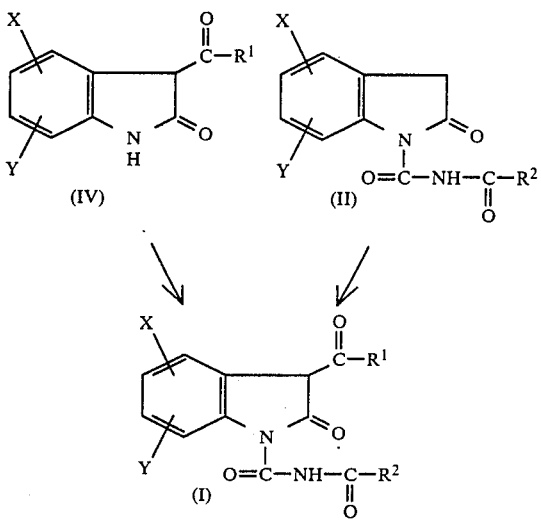

Thus the first variation involves the sequence: compound III to compound IV to compound I, while the second variation involves the sequence: compound III to compound II to compound I.

The —C(=O)—NH—C(=O)—R² group is attached by reacting a compound of the formula III or a compound of the formula IV with an acyl isocyanate of the formula R²—C(=O)—N=C=O. Most commonly, the reaction is carried out by contacting substantially equimolar quantities of the reactants in an inert solvent at a temperature in the range from 50° to 150° C., and preferably from 100° to 130° C. In this context an inert solvent is one which will dissolve at least one of the reactants, and which does not adversely interact with either of the reactants or the product. Typical solvents which can be used include aliphatic hydrocarbons, such as octane, nonane, decane and decalin; aromatic hydrocarbons, such as benzene, chlorobenzene, toluene, xylenes and tetralin; chlorinated hydrocarbons, such as 1,2-dichloroethane; ethers, such as tetrahydrofuran, dioxane, 1,2-dimethoxyethane and di(2-methoxyethyl)ether; and polar, aprotic solvents such as N,N-dimethylformamide, N,N-dimethylacetamide, N-methylpyrrolidone and dimethyl sulfoxide. The reaction time varies according to the reaction temperature, but at a temperature from 100° to 130° C., reaction times of a few hours, e.g., 5 to 10 hours are commonly used.

When a relatively non-polar reaction solvent is used for the reaction of a compound of formula III or IV with an acyl isocyanate of formula R²—C(=O)—N=C=O, the product (I or II) is usually out of solution at the end of the reaction when the reaction mixture is cooled to room temperture. Under these circumstances the product is usually recovered by filtration. However, if relatively polar solvents are used and the product is not out of solution at the end of the reaction, the product can be recovered by solvent evaporation or, in the case of water-miscible solvents, by dilution of the reaction medium with water. This causes the product to precipitate and again it can be recovered by filtration.

The reaction product (I or II) can be purified by standard methods, e.g., recrystallization.

The reaction between a compound of formula IV and an acyl isocyanate of formula R²—C(=O)—N=C=O can be speeded up by the addition of a base, such as a tertiary amine, e.g., trimethylamine, triethylamine, tributylamine, N-methylpiperidine, N-methylmorpholine or N,N-dimethylaniline. From about one to about four equivalents of the basic agent is usually added, and this permits the use of reaction temperature from 20° to 50° C. At the end of the reaction, the reaction medium must be neutralized (or made acidic) and then the product is isolated as described earlier.

The —C(=O)—R¹ side-chain can be attached to a compound of the formula II by reaction with an activated derivative of a carboxylic acid of the formula R¹—C(=O)OH. The reaction is carried out by treating said compound of formula II in an inert solvent with one molar equivalent, or a slight excess, of an activated derivative of a compound of formula R¹—C(=O)OH, in the presence of from one to four equivalents of a basic agent. An inert solvent is one which will dissolve at least one of the reactants, and will not adversely interact with either of the reactants or the product. However, in practice, a polar, aprotic solvent, such as N,N-dimethylformamide, N,N-dimethylacetamide, N-methylpyrrolidone or dimethyl sulfoxide, is commonly used. Conventional methods for activating the acid of formula R¹—C(=O)OH are used. For example, acid halides, e.g., acid chlorides; symmetrical acid anhydrides, R¹—C(=O)—O—C(=O)—R¹; mixed acid anhydrides with a hindered low-molecular weight carboxylic acid, R¹—C(=O)—O—C(=O)—R⁵, where R⁵ is a bulky lower-alkyl group such as t-butyl; and mixed carboxylic-carbonic anhydrides, R¹—C(=O)—O—C(=O)—OR⁶, wherein R⁶ is a lower-alkyl group, can all be used. In addition, N-hydroxyimide esters (such as N-hydroxysuccinimide and N-hydroxyphthalimide esters), 4-nitrophenyl esters, thiol esters (such as thiol phenyl esters) and 2,4,5-trichlorophenyl esters, and the like, can be used.

A wide variety of basic agents can be used in the reaction between a compound of formula II and the activated derivative of the acid of the formula R¹—C(=O)OH. However, preferred basic agents are tertiary amines, such as trimethylamine, triethylamine, tributylamine, N-methylmorpholine, N-methylpiperidine and 4-(N,N-dimethylamino)pyridine.

The reaction between a compound of the formula II and the activated derivative of the acid of formula R¹—C(=O)—OH is usually carried out in the temperature range from −10° to 25° C. Reaction times of from 30 minutes to a few hours are common. At the end of the reaction, the reaction medium is usually diluted with water and acidified, and then the product can be recovered by filtration. It can be purified by standard methods, such as recrystallization.

The —C(=O)—R¹ side-chain can be attached to a compound of the formula III by reaction with a derivative of the appropriate acid of the formula R¹—C(=O)—OH, in a lower-alkanol solvent (e.g. ethanol), in the presence of an alkali metal salt of the lower-alkanol solvent (e.g. sodium ethoxide), according to standard procedures. Typical derivatives of the acid of the formula R¹—C(=O)OH which can be used include acid chlorides, acid anhydrides of the formula R¹—C(=O)—O—(C=O)—R¹, R¹—C(=O)—O—(C=O)—R⁵ and R¹—(C=O)—O—(C=O)—OR⁶, and simple alkyl esters of the formula $R^1$—C(=O)—$OR^6$, wherein $R^5$ and $R^6$ are as defined previously. Usually, a small excess of the derivative of the acid of formula $R^1$—C(=O)—OH is used, and the alkoxide salt is usually present in an amount from one to two molar equivalents, based on said derivative of the acid of formula $R^1$—C(=O)OH. The reaction between the derivative of the acid of the formula $R^1$—C(=O)OH and the compound of formula III is usually started at 0° to 25° C., but it is then usual to heat the reaction mixture at a temperature in the range from 50° to 130° C., and preferably at about 80° C., to complete the reaction. Under these circumstances, reaction times of a few hours, e.g. two hours, up to a few days, e.g., two days, are commonly used. The reaction mixture is then cooled, diluted with an excess of water, and acidified. The product of formula IV can then be recovered by filtration or by the standard procedure of solvent extraction.

The acyl isocyanates of the formula $R^2$—C(=O)—N=C=O which are known can be prepared by the published procedures. Those which are analogs of known compounds can be prepared by analogous procedures. In general, the corresponding amide of the formula $R^2$—C(=O)—$NH_2$ reacts with oxalyl chloride, or the acid chloride of formula $R^2$—C(=O)—Cl reacts with silver cyanate. Consult: Speziale et al., *Journal of Organic Chemistry*, 28, 1805 (1963) and 30, 4306 (1965); Ramirez et al., *Journal of Organic Chemistry*, 34, 376 (1969); and Naito et al., *Journal of Antibiotics* (Japan), 18, 145 (1965).

The 2-oxindole compounds of formula III are prepared by known methods, or methods analogous to known methods. Consult: "Rodd's Chemistry of Carbon Compounds," Second Edition, S. Coffey editor, Volume IV Part A, Elsevier Scientific Publishing Company, 1973, pp. 448-450; Gassman et al., *Journal of Organic Chemistry*, 42, 1340 (1977); Wright et al., *Journal of the American Chemical Society*, 78, 221 (1956); Beckett et al., *Tetrahedron*, 24, 6093 (1968); U.S. Pat. Nos. 3,882,236, 4,006,161 and 4,160,032; Walker, *Journal of the American Chemical Society*, 77, 3844 (1955); Protiva et al., *Collection of Czechoslovakian Chemical Communications*, 44, 2108 (1979); McEvoy et al., *Journal of Organic Chemistry*, 38, 3350 (1973); Simet, *Journal of Organic Chemistry*, 28, 3580 (1963); Wieland et al., *Chemische Berichte*, 96, 253 (1963); and references cited therein.

The compounds of the formula I are acidic and they form base salts. All such base salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, as appropriate, or, in the case of aqueous solutions, by lyophilization. Typical salts of the compounds of formula I which can be prepared are primary, secondary and tertiary amine salts, alkali metal salts and alkaline earth metal salts. Especially valuable are the ethanolamine, diethanolamine and triethanolamine salts.

Basic agents suitably employed in salt formation belong to both the organic and inorganic types, and they include organic amines, alkali metal hydroxides, alkali metal carbonates, alkali metal bicarbonates, alkali metal hydrides, alkali metal alkoxides, alkaline earth metal hydroxides, alkaline earth metal carbonates, alkaline earth metal hydrides and alkaline earth metal alkoxides. Representative examples of such bases are primary amines, such as n-propylamine, n-butylamine, aniline, cyclohexylamine, benzylamine, p-toluidine, ethanolamine and glucamine; secondary amines, such as diethylamine, diethanolamine, N-methylglucamine, N-methylaniline, morpholine, pyrrolidine and piperidine; tertiary amines, such as triethylamine, triethanolamine, N,N-dimethylaniline, N-ethylpiperidine and N-methylmorpholine; hydroxides, such as sodium hydroxide; alkoxides, such as sodium ethoxide and potassium methoxide; hydrides, such as calcium hydride and sodium hydride; and carbonates, such as potassium carbonate and sodium carbonate.

The compounds of formula I possess analgesic activity. This activity has been demonstrated in mice by showing blockade of the abdominal stretching induced by administration of 2-phenyl-1,4-benzoquinone (PBQ). The method used was based on that of Siegmund et al., *Proc. Soc. Exp. Biol. Med.*, 95: 729-731, 1957, as adapted for high throughput (see further Milne and Twomey, *Agents and Actions*, 10: 31-37, 1980). The mice used in these experiments were Carworth males, albino CF-1 strain, weighing 18-20 g. All mice were fasted overnight prior to drug administration and testing.

The compounds of formula I were dissolved or suspended in a vehicle consisting of ethanol (5%), emulphor 620 (a mixture of polyoxyethylene fatty acid esters, 5%) and saline (90%). This vehicle also served as control. Doses were on a logarithmic scale (i.e., ... 0.32, 1.0, 3.2, 10, 32 ... mg/kg), and were calculated from weights of the salt when applicable, and not of the acid. The route of administration was oral, with concentrations varied to allow a constant dosage volume of 10 ml/kg of body weight. The aforesaid method of Milne and Twomey was used to determine efficacy and potency. Mice were treated with compounds orally, and one hour later received PBQ, 2 mg/kg, intraperitoneally. Individual mice were then immediately placed in a warmed Lucite (transparent plastic) chamber, and, starting five minutes after PBQ administration, the number of abdominal constrictions during the subsequent 5 minutes was recorded. The degree of analgesic protection (% MPE) was calculated on the basis of suppression of abdominal constriction relative to counts from concurrent control animals run on the same day. At least four such determinations (N≧5) provided dose-response data for generation of an $MPE_{50}$, the best estimate of the dose that reduces abdominal constriction to 50% of control levels.

The compounds of formula I also possess antiinflammatory activity. This activity has been demonstrated in rats by a method based on the standard carrageenin-induced rat-foot edema test. (Winter et al., *Proc. Soc. Exp. Biol. Med.*, 111: 544, 1963).

Unanesthetized, adult, male, albino rats of 150 g to 190 g body weight were numbered, weighed, and an ink mark placed on the right lateral malleolus. Each paw was immersed in mercury exactly to the ink mark. The mercury was contained in a glass cylinder, connected to a Statham Pressure Transducer. The output from the transducer was fed through a control unit to a microvoltameter. The volume of mercury displaced by the immersed paw was read. Drugs were given by gavage. One hour after drug administration, edema was induced by injection of 0.05 ml of 1% solution of carrageenin into the plantar tissue of the marked paws. Immediately thereafter, the volume of the injected foot was measured. The increase in foot volume 3 hours after the injection of carrageenin constitutes the individual inflammatory response.

The analgesic activity of the compounds of formula I makes them useful for acute administration to mammals for the control of pain, e.g., post-operative pain and the pain of trauma. Additionally the compounds of formula I are useful for chronic administration to mammals for the alleviation of the symptoms of chronic diseases, such as the inflammation of rheumatoid arthritis, and the pain associated with osteoarthritis and other musculoskeletal disorders.

When a compound of the formula I or a pharmaceutically acceptable salt thereof is to be used as either an analgesic agent or an anti-inflammatory agent, it can be administered to a mammalian subject either alone, or, preferably, in combination with pharmaceutically-acceptable carriers or diluents in a pharmaceutical composition, according to standard pharmaceutical practice. A compound can be administered orally or parenterally. Parenteral administration includes intravenous, intramuscular, intraperitoneal, subcutaneous and topical administration.

In a pharmaceutical composition comprising a compound of formula I, or a pharmaceutically-acceptable salt thereof, the weight ratio of carrier to active ingredient will normally be in the range from 1:4 to 4:1, and preferably 1:2 to 2:1. However, in any given case, the ratio chosen will depend on such factors as the solubility of the active component, the dosage contemplated and the precise route of administration.

For oral use of a compound of formula I of this invention, the compound can be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents are lactose and dried corn starch. When aqueous suspensions are required for oral use, the active ingredient is combined with emulsifying and suspending agents. If desired, certain sweetening and/or flavoring agents can be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled to render the preparation isotonic.

When a compound of formula I or salt thereof is used in a human subject, the daily dosage will normally be determined by the prescribing physician. Moreover, the dosage will vary according to the age, weight and response of the individual patient, as well as the severity of the patient's symptoms and the potency of the particular compound being administered. However, for acute administration to relieve pain, an effective analgesic response eliciting dose in most instances will be 0.1 to 1.0 g as needed. (e.g., every four to six hours). For chronic administration to alleviate (treat) inflammation and pain, in most instances an effective dose will be from 0.5 to 3.0. g per day, and preferably 0.5 to 1.5 g per day, in single or divided doses. On the other hand, it may be necessary to use dosages outside these limits in some cases.

The following examples and preparations are being provided solely for the purpose of further illustration.

EXAMPLE 1

N-Benzoyl-3-(2-furoyl)-2-oxindole-1-carboxamide

A mixture of 909 mg (4.0 mmole) of 3-(2-furoyl)-2-oxindole and 706 mg (4.8 mmole) of benzoyl isocyanate in 25 ml of toluene was heated to reflux and then it was heated at reflux temperature for 7 hours. The mixture was allowed to stand at room temperature overnight and then the precipitate which had formed was removed by filtration, giving 1.3 g of crude product. The crude product was recrystallized from ca 30 ml of acetic acid, giving 920 mg of the title compound, mp 184° C. (dec).

Analysis: Calcd. for $C_{21}H_{14}O_5N_2$: C, 67.37; H, 3.77; N, 7.49%.. Found: C, 66.90; H, 4.02; N, 7.38%.

EXAMPLE 2

N-Benzoyl-3-(2-furoyl)-2-oxindole-1-carboxamide

To 30 ml of N,N-dimethylformamide was added, with stirring, 2.8 g (10 mmole) of N-benzoyl-2-oxindole-1-carboxamide, followed by 2.9 g (24 mmole) of 4-(N,N-dimethylamino)pyridine. The mixture was cooled in an ice-bath and then to it was added, dropwise, with stirring, during 10 minutes, a solution of 1.6 g (12 mmole) of 2-furoyl chloride in 10 ml of N,N-dimethylformamide. Stirring was continued for 30 minutes and then the reaction mixture was poured into a mixture prepared from 250 ml of water and 8.5 ml of 3 N hydrochloric acid. The resulting mixture was cooled in an ice-bath and the solid was removed by filtration. The solid was recrystallized from ca. 75 ml of acetic acid to give 2.94 g of the title compound as yellow-brown crystals, mp 190° C.

The ultraviolet spectrum of the title compound showed absorptions as follows:

| Solvent | Wavelength (nanometers) | Epsilon |
|---|---|---|
| $CH_3OH$ | 245 | 6,920 |
|  | 375 | 2,530 |
| $CH_3OH$ + 1 drop 0.1 N NaOH | 249 | 7,200 |
|  | 372 | 2,710 |
| $CH_3OH$ + 1 drop 0.1 N HCl | 241 | 9,070 |

EXAMPLE 3

N-Benzoyl-3-acetyl-2-oxindole-1-carboxamide

To a stirred slurry of 841 mg (3.0 mmole) of N-benzoyl-2-oxindole-1-carboxamide in 5 ml of N,N-dimethylformamide was added 806 mg (6.6 mmole) of 4-(N,N-dimethylamino)pyridine. Stirring was continued for a few minutes, and then the slurry was cooled in an ice-bath and a solution of 337 mg (3.3 mmole) of acetic anhydride in 2 ml of N,N-dimethylformamide was added dropwise. Stirring was continued for 1 hour, and then the reaction mixture was poured onto a mixture of 65–70 ml. of ice-water and 2.2 ml of 3 N hydrochloric acid. The solid which precipitated was recovered by filtration. It was recrystallized from ethanol to give 385 mg of the title compound as tan crystals, mp 198° C.

Analysis Calcd. for $C_{18}H_{14}O_4N_2$: C, 67.07; H, 4.38; N, 8.69%. Found: C, 66.78; H, 4.65; N, 8.62%.

EXAMPLE 4

N-Benzoyl-3-(2-thenoyl)-2-oxindole-1-carboxamide

To a stirred solution of 486 mg (2.0 mmole) of 3-(2-thenoyl)-2-oxindole and 445 mg (4.4 mmole) of triethylamine in 5 ml of dimethyl sulfoxide was added 324 mg (2.2 mmole) of benzoyl isocyanate. Stirring was continued for 1 hour, and then the mixture was poured into a mixture of 50 ml of water and 1.7 ml of 3 N hydrochloric acid. The resulting mixture was cooled in an ice-bath and the solid was removed by filtration. The solid was recrystallized from ca. 30 ml of 2:1 ethanol:water to give 190 mg of the title compound as fluffy, yellow crystals, mp 165°–166° C. (dec).

Analysis: Calcd. for $C_{21}H_{14}O_4N_2S$: C, 64.60; H, 3.61; N, 7.18%. Found: C, 64.53; H, 3.75; N, 7.10%.

EXAMPLE 5

Reaction of the appropriate N-substituted-2-oxindole-1-carboxamide with the requisite acid chloride of the formula $R^1$—CO—Cl, substantially according to the procedure of Example 2, afforded the following compounds:

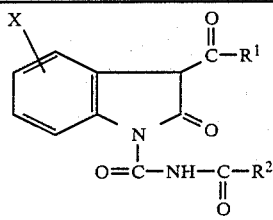

| X | $R^1$ | $R^2$ | Melting Point (°C.)[1] | Analysis Calculated C | H | N | Found C | H | N |
|---|---|---|---|---|---|---|---|---|---|
| H | 2-thienyl | phenyl | 165–166 | 64.60 | 3.61 | 7.18 | 64.53 | 3.75 | 7.10 |
| H | (2-thienyl)-methyl | phenyl | 188–190 | 65.33 | 3.99 | 6.93 | 65.39 | 3.93 | 6.96 |
| 5-Cl | 2-furyl | phenyl | 206–208 | 61.70 | 3.20 | 6.85 | 61.54 | 3.21 | 6.71 |
| 5-Cl | 2-thienyl | phenyl | 190–192 | 59.37 | 3.08 | 6.59 | 59.12 | 3.32 | 6.59 |
| 5-Cl | (2-thienyl)-methyl | phenyl | 213–214 | 60.21 | 3.44 | 6.38 | 60.35 | 3.62 | 6.37 |
| H | 2-furyl | cyclohexyl | 178.5 | 66.30 | 5.30 | 7.37 | 66.09 | 5.24 | 7.22 |
| H | 2-thienyl | cyclohexyl | 143.5–144.5 | 63.62 | 5.09 | 7.07 | 63.45 | 5.27 | 7.11 |
| H | (2-thienyl)-methyl | cyclohexyl | 175.5–176.5 | 64.37 | 5.40 | 6.83 | 64.60 | 5.49 | 6.74 |
| 5-Cl | 2-furyl | cyclohexyl | 185–186 | 60.80 | 4.62 | 6.75 | 60.59 | 4.88 | 6.77 |
| 5-Cl | 2-thienyl | cyclohexyl | 167 | 58.54 | 4.44 | 6.50 | 58.41 | 4.60 | 6.52 |
| 5-Cl | (2-thienyl)-methyl | cyclohexyl | 181–183 | 59.39 | 4.76 | 6.30 | 58.97 | 5.03 | 6.23 |
| H | 2-furyl | t-butyl | 201.5 | 64.40 | 5.12 | 7.91 | 64.24 | 5.11 | 7.97 |
| H | 2-thienyl | t-butyl | 177.5 | 61.60 | 4.90 | 7.56 | 61.72 | 4.95 | 7.60 |
| H | (2-thienyl)-methyl | t-butyl | 192[2] | 62.48 | 5.24 | 7.29 | 62.59 | 5.29 | 7.48 |
| 5-Cl | 2-furyl | t-butyl | 191 | 58.69 | 4.41 | 7.21 | 58.56 | 4.45 | 7.05 |
| 5-Cl | 2-thienyl | t-butyl | 200.5 | 56.36 | 4.23 | 6.92 | 56.55 | 4.19 | 7.05 |
| 5-Cl | (2-thienyl)-methyl | t-butyl | 155 | 57.34 | 4.57 | 6.69 | 57.28 | 4.58 | 6.55 |
| H | 2-furyl | isopropyl | 191.5 | 63.52 | 4.74 | 8.23 | 63.30 | 4.73 | 8.23 |
| H | 2-thienyl | isopropyl | 153.5–154.5 | 60.66 | 4.53 | 7.86 | 60.91 | 4.75 | 7.98 |
| H | (2-thienyl)-methyl | isopropyl | 156–157[3] | 61.60 | 4.90 | 7.56 | 61.59 | 5.01 | 7.56 |
| 5-Cl | 2-furyl | isopropyl | 176–177 | 57.69 | 4.03 | 7.47 | 57.68 | 4.08 | 7.37 |
| 5-Cl | 2-thienyl | isopropyl | 165–166[2,3] | 55.32 | 3.87 | 7.17 | 55.19 | 3.89 | 7.14 |
| 5-Cl | (2-thienyl)-methyl | isopropyl | 168–169[3] | 56.37 | 4.23 | 6.92 | 56.17 | 4.41 | 6.97 |

[1]All compounds were recrystallized from acetic acid and melted with decomposition unless noted otherwise.
[2]Recrystallized from acetonitrile.
[3]Melted without decomposition.

EXAMPLE 6

N-Benzoyl-3-(2-thenoyl)-2-oxindole-1-carboxamide was also prepared by reaction of 3-(2-thenoyl)-2-oxindole with benzoyl isocyanate using the method of Example 1.

N-Benzoyl-3-(2-[2-thienyl]acetyl)-2-oxindole-1-carboxamide was prepared by reaction of 3-(2-[2thienyl]acetyl)-2-oxindole with benzoyl isocyanate using the method of Example 1.

EXAMPLE 7

Following the method of Example 1 (Method A), Example 2 or 3 (Method B), or Example 4 (Method C), the following compounds were made:

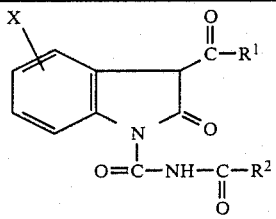

| X | $R^1$ | $R^2$ | Method of Preparation[1] | Melting Point (°C.)[2] |
|---|---|---|---|---|
| H | methyl | phenyl | A,B | 198–200d |
| H | isopropyl | phenyl | B | 165d |
| H | cyclohexyl | phenyl | B | 181d |
| 5-Cl | methyl | phenyl | B | 215–217d |
| 5-Cl | isopropyl | phenyl | B | 185.5–187.5d |
| 5-Cl | cyclohexyl | phenyl | B | 192–194d |
| H | phenoxymethyl | phenyl | A | 202d |
| H | 3-furyl | phenyl | C | 187d |
| 5-Cl | cyclopropyl | phenyl | B | 213–215d |
| H | cyclopropyl | phenyl | B | 173d |
| H | isopropyl | phenyl | B | 165d |
| H | 1-phenylethyl | phenyl | B | 173d |
| 5-Cl | benzyl | phenyl | B | 239–240d |
| 5-$CH_3$ | 2-furyl | phenyl | B | 204–205d |

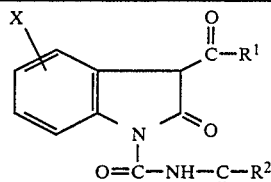

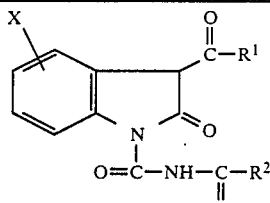

| X | R¹ | R² | Method of Preparation[1] | Melting Point (°C.)[2] |
|---|---|---|---|---|
| H | (3-thienyl)-methyl | phenyl | B | 195–197d |
| 6-Cl | 2-thienyl | phenyl | B | 192–193d |
| 6-F | 2-furyl | phenyl | B | 189–190 |
| 6-F | 2-thienyl | phenyl | B | 190–194 |
| 5-Cl | 5-ethyl-2-furyl | phenyl | B | 202–203.5d |
| H | 5-ethyl-2-furyl | phenyl | B | 174–175 |
| 5-F | 2-furyl | phenyl | B | 172d |
| 5-F | (2-thienyl)-methyl | phenyl | B | 189d |
| 6-Cl | 2-furyl | phenyl | B | 199–200 |
| 5-F | (2-thienyl)-methyl | phenyl | B | 167d |
| 6-Cl | (2-thienyl)-methyl | phenyl | B | 199–200d |
| H | 2-thienyl | 4-fluoro-phenyl | C | 163.5–164.5d |
| H | 2-furyl | 4-fluoro-phenyl | C | 164.5d |
| H | methyl | 4-fluoro-phenyl | A | 205–207d |
| H | benzyl | 4-fluoro-phenyl | A | 207–209d |
| H | cyclopropyl | 4-fluoro-phenyl | B | 167.5d |
| H | (2-thienyl)-methyl | 4-fluoro-phenyl | A | 216–217d |
| 5-CH₃ | 2-thienyl | 4-fluoro-phenyl | B | 178–179d |
| 5-Cl | 2-furyl | 4-fluoro-phenyl | B | 197–199d |
| 5-CH₃ | 2-furyl | 4-fluoro-phenyl | B | 179–181d |
| 5-Cl | 2-thienyl | 4-fluoro-phenyl | B | 191.5–192.5d |
| H | (2-thienyl)-methyl | 4-methoxy-phenyl | A | 197–198d |
| H | 2-thienyl | 4-methoxy-phenyl | B | 173d |
| H | 2-furyl | 4-methoxy-phenyl | B | 146d |
| H | cyclopropyl | 4-methoxy-phenyl | B | 193d |
| H | isopropyl | 4-methoxy-phenyl | B | 125d |
| H | 2-furyl | 4-chloro-phenyl | B | 180–181d |
| H | 2-thienyl | 4-chloro-phenyl | B | 170–171d |
| H | isopropyl | 4-chloro-phenyl | B | 164–165d |
| H | propyl | 4-chloro-phenyl | B | 184–185d |
| H | 2-thienyl | 2-methyl-phenyl | B | 173.5d |
| H | 2-furyl | 2-methyl-phenyl | B | 167–168d |
| H | (2-thienyl)-methyl | 2-methyl-phenyl | B | 179.5d |
| H | cyclopropyl | cyclohexyl | B | 153–154d |
| H | methyl | cyclohexyl | B | 167–168d |
| H | 1-phenylethyl | cyclohexyl | B | 191d |
| H | 5-methyl-2-furyl | cyclohexyl | B | 163–165d |
| 5-Cl | 5-methyl-2-furyl | cyclohexyl | B | 197.5d |
| 5-Cl | methyl | cyclohexyl | B | 214.5d |
| 5-Cl | propyl | cyclohexyl | B | 162–163d |
| 5-Cl | isopropyl | cyclohexyl | B | 205–206d |
| 5-CH₃ | 2-furyl | cyclohexyl | B | 170–171 |
| 5-CH₃ | 2-thienyl | cyclohexyl | B | 153–154.5d |
| H | 5-ethyl-2-furyl | cyclohexyl | B | 146–147 |
| 5-CH₃ | 5-ethyl-2-furyl | cyclohexyl | B | 190–191 |
| 5-CH₃ | (2-thienyl)-methyl | cyclohexyl | B | 158–159 |
| 5-Cl | 5-ethyl-2-furyl | cyclohexyl | B | 210–211d |
| 6-Cl | 2-furyl | cyclohexyl | B | 183–184 |
| 5-F | 2-furyl | cyclohexyl | B | 186.5–187.5d |
| 5-F | 2-thienyl | cyclohexyl | B | 145.5–146.5d |
| 5-F | (2-thienyl)-methyl | cyclohexyl | B | 164–165 |
| 6-Cl | 2-thienyl | cyclohexyl | B | 172–173 |
| 6-Cl | (2-thienyl)-methyl | cyclohexyl | B | 173–175d |
| 4-Cl | 2-thienyl | cyclohexyl | B | 189–190 |
| 4-Cl | (2-thienyl)-methyl | cyclohexyl | B | 172–173 |
| 4-Cl | methyl | cyclohexyl | B | 131–132 |
| 5-CF₃ | 2-furyl | cyclohexyl | B | 194–195d |
| 5-CF₃ | 2-thienyl | cyclohexyl | B | 171–172d |
| 6-F | 2-furyl | cyclohexyl | B | 164–166 |
| 6-F | 2-thienyl | cyclohexyl | B | |
| 5-CH₃ | 2-thienyl | t-butyl | B | 189.5d |
| 5-CH₃ | methyl | t-butyl | B | 194d |
| 5-Cl | methyl | t-butyl | B | 211.5d |
| 5-CH₃ | 5-ethyl-2-furyl | t-butyl | B | 214–215 |
| 5-Cl | 5-ethyl-2-furyl | t-butyl | B | 224–225 |
| 5-F | 2-furyl | t-butyl | B | 212.5d |
| 5-F | 2-thienyl | t-butyl | B | 183.5d |
| 5-F | (2-thienyl)-methyl | t-butyl | B | 161d |
| 6-Cl | 2-thienyl | t-butyl | B | 191–192 |
| 5-CH₃ | 2-thienyl | isopropyl | B | 146–147d |
| 5-CH₃ | 2-furyl | isopropyl | B | 166–167d |
| 5-CH₃ | phenoxymethyl | isopropyl | B | 184–186 |
| 5-Cl | phenoxymethyl | isopropyl | B | 186–188d |
| 5-Cl | benzyl | isopropyl | B | 184–185 |
| 5-Cl | cyclohexyl | isopropyl | B | 206–208d |
| 5-CH₃ | 5-methyl-2-furyl | isopropyl | B | 194d |
| 5-CH₃ | methyl | isopropyl | B | 158–159 |
| 5-Cl | 5-methyl-2-furyl | isopropyl | B | 198.5–199.5 |
| 5-Cl | methyl | isopropyl | B | 215–216 |
| H | methyl | isopropyl | B | 170–172 |
| H | cyclohexyl | isopropyl | B | 188–189 |
| H | benzyl | isopropyl | B | 145–146 |
| H | phenoxymethyl | isopropyl | B | 157–158 |
| 5-Cl | 5-ethyl-2-furyl | isopropyl | B | 209–211d |
| 5-Cl | isopropyl | isopropyl | B | 142–143 |
| 6-Cl | 2-furyl | isopropyl | B | 184–185d |
| 6-Cl | 2-thienyl | isopropyl | B | 174.5–175 |
| 6-Cl | (2-thienyl)-methyl | isopropyl | B | 157–158d |
| H | 2-thienyl | phenoxymethyl | B | 161–162 |
| 5-Cl | 2-thienyl | phenoxymethyl | B | 182–183 |
| H | 2-furyl | phenoxymethyl | B | 173–175d |
| H | (2-thienyl)-methyl | phenoxymethyl | B | 193–194 |
| 5-Cl | 2-furyl | phenoxymethyl | B | 194–195.5 |

[1] The letter A in this column indicates that the compound was prepared substantially according to Example 1; the letter B indicates that the compound was prepared substantially according to Example 2 or 3; and the letter C indicates that the compound was prepared substantially according to Example 4.
[2] The letter "d" indicates that the compound melted with decomposition.

EXAMPLE 8

By reaction of the appropriate acid chloride with the requisite N-substituted-2-oxindole-1-carboxamide, using the procedure of Example 2, the following compounds can be prepared:

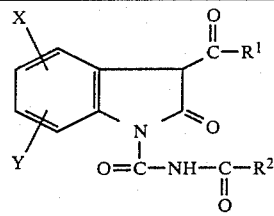

| X | Y | R¹ | R² |
|---|---|---|---|
| H | H | hexyl | 3-butoxyphenyl |
| 5-Br | H | cycloheptyl | 4-isobutylphenyl |
| H | 5-Br | cyclohexyl | methyl |
| n-C$_4$H$_9$ | H | phenyl | ethyl |
| H | 5-C$_2$H$_5$O | 2-thienyl | hexyl |
| 6-n-C$_4$H$_9$O | H | 2-furyl | cyclopropyl |
| H | 5-n-C$_4$H$_9$O | 3-thienyl | cyclopentyl |
| 5-CH$_3$O | 6-CH$_3$O | ethyl | cyclohexyl |
| 7-Cl | H | phenyl | propyl |
| 4-CH$_3$S | H | 5-methylhexyl | phenyl |
| H | 6-CH$_3$S | ethyl | 3-chlorophenyl |
| 5-n-C$_4$H$_9$S | H | cyclohexyl | 3-fluorophenyl |
| H | H | 3-phenylpropyl | cycloheptyl |
| 5-Cl | H | 3-phenoxypropyl | butyl |
| 5-F | H | 5-propyl-2-furyl | phenyl |
| 5-CH$_3$ | H | 4-methyl-2-thienyl | cyclohexyl |
| H | H | 3-methyl-2-thienyl | 4-ethylphenyl |
| 4-Cl | H | 5-propyl-2-thienyl | phenyl |
| 6-Cl | H | (2-furyl)methyl | cyclobutyl |
| 6-Cl | H | 3-(2-furyl)propyl | pentyl |
| 5-F | H | 2-(2-thienyl)ethyl | 4-chlorophenyl |
| 6-Cl | H | 3-(2-thienyl)propyl | 4-methoxyphenyl |
| H | H | 1-naphthyl | phenyl |
| 5-Cl | H | 2-naphthyl | cyclohexyl |
| 5-CH$_3$ | H | 2-benzo[b]furyl | hexyl |
| 5-F | H | 3-benzo[b]furyl | phenyl |
| H | H | 2-benzo[b]thienyl | cyclohexyl |
| 5-CH$_3$ | H | 3-benzo[b]thienyl | hexyl |
| H | H | ethyl | 3,4-dichlorophenyl |
| 4-CH$_3$ | 5-CH$_3$ | phenyl | cyclohexyl |
| 5-Cl | H | 2-thienyl | 3,4-diethoxyphenyl |
| 5-CH$_3$ | 6-CH$_3$ | cyclopentyl | phenyl |
| 5-F | H | 2-furyl | 3-fluoro-4-chlorophenyl |
| 5-OCH$_3$ | H | butyl | cyclobutyl |
| 5-CF$_3$ | H | (2-thienyl)methyl | 2,4-difluorophenyl |
| 6-Cl | H | 2-naphthyl | 3,5-dichlorophenyl |
| 6-Br | H | benzyl | ethyl |
| H | H | 2-furyl | 3-ethoxy-4-butoxyphenyl |
| 5-Cl | 6-Cl | 2-thienyl | 4-methoxyphenyl |
| 6-F | H | hexyl | cyclohexyl |
| 5-F | 6-Cl | 2-thienyl | 2,4-dimethylphenyl |
| 6-CF$_3$ | H | 2-furyl | 4-chlorophenyl |
| 5-CH$_3$ | 6-F | cyclohexyl | 3,5-dimethylphenyl |
| 6-OCH$_3$ | H | 2-furyl | cycloheptyl |
| H | H | 2-thienyl | 4-trifluoromethylphenyl |
| 5-Cl | H | 2-pyrrolyl | phenyl |
| 5-CH$_3$SO | H | 2-thienyl | phenyl |
| 5-n-C$_4$H$_9$SO | H | 2-furyl | cyclohexyl |
| 4-CH$_3$SO$_2$ | H | 3-fluorophenyl | phenoxymethyl |
| 5-n-C$_4$H$_9$SO$_2$ | H | 2-thiazolyl | phenyl |
| 5-NO$_2$ | H | 2-(3-thienyl)ethyl | cyclohexyl |
| 6-C$_6$H$_5$ | H | 4-chlorophenyl | 2-furyl |
| H | 5-Br | 2-(2-tolyl)ethyl | cyclohexyl |
| 5-CH$_3$CO | H | 4-trifluoromethylphenyl | phenyl |
| 6-n-C$_3$H$_7$CO | H | 4-isothiazolyl | n-hexyl |
| 5-Cl | H | 1-naphthyl | 3-thienyl |
| 5-C$_6$H$_5$CO | H | 1,2,3-thiadiazol-4-yl | cyclohexyl |
| 5-C$_4$H$_3$SCO¹ | H | 3-(3-chlorophenyl)propyl | 3-methylphenyl |
| 6-CF$_3$ | H | (4-thiazolyl)methyl | 4-chlorophenyl |
| 6-F | H | 1,2,5-thiadiazol-3-yl | cyclohexyl |
| 5-CH$_3$CONH | H | 1-methyl-1-phenylethyl | ethyl |
| 5-Cl | 6-Cl | 5-methyl-4-isoxazolyl | 4-methoxyphenyl |
| 5-(CH$_3$)$_2$CHCONH | H | 2-(4-isopropylphenyl)ethyl | phenyl |
| 5-C$_6$H$_5$CONH | H | 2-thienyl | phenyl |
| 5-CH$_3$ | 6-CH$_3$ | 4-isopropoxyphenyl | 3-pyridyl |
| 5-SO$_2$N(CH$_3$)$_2$ | H | benzyl | phenyl |
| 5-F | 6-F | 4-chlorophenoxy | 2-methylphenyl |
| 5-SO$_2$N(n-C$_3$H$_7$)$_2$ | H | 2-tetrahydrofuryl | n-hexyl |
| H | 4-Cl | 4-pyridyl | phenyl |
| 6-Cl | H | 3-tetrahydrothienyl | 3,5-dichlorophenyl |

-continued

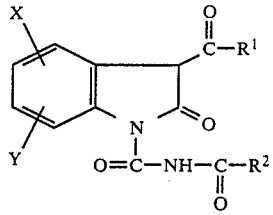

| X | Y | R¹ | R² |
|---|---|----|----|
| H | H | 5-pyrimidyl | cyclohexyl |
| 5-CH₃ | 6-F | 2-pyrazinyl | 3,5-dimethylphenyl |
| H | H | 2-n-propyl-4-thiazolyl | phenyl |
| 5-Br | H | 2-oxazolyl | 4-isobutylphenyl |
| H | H | 3-isoxazolyl | phenyl |

$^1$5-(2-thenoyl)

EXAMPLE 9

By reaction of 2-furoyl chloride with N-benzoyl-5,6-methylenedioxy-2-oxindole-1-carboxamide, N-cyclohexylcarbonyl-5,6-ethylenedioxy-2-oxindole-1-carboxamide, N-benzoyl-5-cyclopropyl-2-oxindole-1-carboxamide and N-isobutyryl-5-cycloheptyl-2-oxindole-1-carboxamide, respectively, using the method of Example 2, the following compounds can be prepared:
N-benzoyl-3-(2-furoyl)-5,6-methylenedioxy-2-oxindole-1-carboxamide,
N-cyclohexylcarbonyl-3-(2-furoyl)-5,6-ethylenedioxy-2-oxindole-1-carboxamide,
N-benzoyl-3-(2-furoyl)-5-cyclopropyl-2-oxindole-1-carboxamide and
N-isobutyryl-3-(2-furoyl)-5-cycloheptyl-2-oxindole-1-carboxamide, respectively.

EXAMPLE 10

The compounds in the Table below can be prepared by reaction of the appropriate acid chloride with the requisite N-substituted-2-oxindole-1-carboxamide, using the procedure of Example 2.

| X and Y* | R¹ | R² |
|----------|----|----|
| 4-CH₂—CH₂—CH₂—5 | 2-furyl | phenyl |
| 5-CH₂—CH₂—CH₂—6 | 2-thienyl | cyclohexyl |
| 6-CH₂—CH₂—CH₂—CH₂—7 | 2-furyl | 4-fluorophenyl |
| 5-CH=CH—CH=CH—6 | (2-thienyl)methyl | t-butyl |
| 5-O—CH₂—CH₂—6 | 2-thienyl | isopropyl |
| 5-CH₂—CH₂—O—6 | 2-furyl | phenyl |
| 5-S—CH₂—CH₂—6 | 2-thienyl | cyclohexyl |
| 5-O—CH=CH—6 | 2-furyl | t-butyl |
| 5-S—CH=CH—6 | (2-thienyl)methyl | cyclohexyl |
| 5-CH=CH—S—6 | 2-furyl | phenyl |

*In this column, the numeral to the left of the formula indicates the point attachment of that end of the formula to the 2-oxindole nucleus and the numeral to the right indicates the point of attachment of that end of the formula to the 2-oxindole nucleus.

EXAMPLE 11

Ethanolamine Salt of N-Benzoyl-3-(2-furoyl)-2-oxindole-1-carboxamide

To a slurry of 562 mg (1.5 mmole) of N-benzoyl-3-(2-furoyl)-2-oxindole-1-carboxamide in 10 ml of methanol was added 101 mg (1.65 mmole) of ethanolamine. The resulting mixture was heated to boiling for a few minutes and then it was allowed to cool. The solid which precipitated was recovered by filtration to give 524 mg of the title salt, mp 165°–166° C. Yield: 80%.

Analysis: Calcd. for $C_{23}H_{21}O_6N_3$: C, 63.44; H, 4.86; N, 9.65%. Found: C, 63.27; H, 4.95; N, 9.58%.

EXAMPLE 12

The diethanolamine salt of N-benzoyl-3-(2-furoyl)-2-oxindole-1-carboxamide was prepared by substituting diethanolamine for ethanolamine in the procedure of Example 11. The product melted at 157°–158° C. Yield: 74%.

Analysis: Calcd. for $C_{25}H_{25}O_7N_3$: C, 62.62; H, 5.26; N, 8.76%. Found: C, 62.53; H, 5.31; N, 8.74%.

EXAMPLE 13

The triethanolamine salt of N-benzoyl-3-(2-furoyl)-2-oxindole-1-carboxamide was prepared by substituting triethanolamine for ethanolamine in the procedure of Example 11. The product melted at 154°–155° C. Yield: 60%.

Analysis: Calcd. for $C_{27}H_{29}O_8N_3$: C, 61.94; H, 5.58; N, 8.03%. Found: C, 61.84; H, 5.61; N, 7.99%.

EXAMPLE 14

N-Benzoyl-2-oxindole-1-carboxamide

To a stirred slurry of 399 mg (3.0 mmole) of 2-oxindole in 7 ml of toluene was added 485 mg (3.3 mmole) of benzoyl isocyanate. The mixture was heated under reflux for 2.2 hours and then it was cooled to room temperature. The solid was recovered by filtration and it was then dissolved in ca. 10 ml of hot acetonitrile. The acetonitrile solution was decolorized using activated carbon and then allowed to cool and the precipitate was recovered by filtration. Recrystallization of the precipitate from acetonitrile gave 131 mg of the title compound, mp 183.5°–184.5° C.

Analysis: Calcd. for $C_{16}H_{12}O_3N_2$: C, 68.56; H, 4.32; N, 9.99%. Found: C, 68.37; H, 4.58; N, 10.16%.

EXAMPLE 15

Reaction of the appropriate 2-oxindole with the requisite acyl isocyanate, substantially according to the precedure of Example 14, afforded the following compounds:

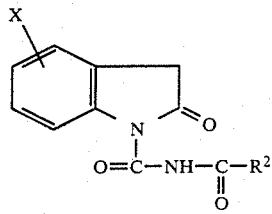

| X | R² | Melting Point(0° C.)[1] | Yield(%) |
|---|---|---|---|
| 5-Cl | phenyl | 193–195 | 43 |
| 5-CH₃ | phenyl | 202–203 | 68 |
| 6-Cl | phenyl | 206–207 | 59 |
| 6-F | phenyl | 174–175.5 | |
| 5-F | phenyl | 187d | 37 |
| H | 4-fluorophenyl | 177–178d | 21 |
| 5-CH₃ | 4-fluorophenyl | 209–211d | 78 |
| 5-Cl | 4-fluorophenyl | 198–199d | 59 |
| H | 4-methoxyphenyl | 180d | 72 |
| H | 4-chlorophenyl | 186.5–187.5d | 53 |
| H | 2-methylphenyl | 166.5–167.5 | 59 |
| H | cyclohexyl | 144.5–145.5 | 62 |
| 5-Cl | cyclohexyl | 172–174 | 63 |
| 5-CH₃ | cyclohexyl | 140–141.5 | 68 |
| 6-Cl | cyclohexyl | 181–182 | 56 |
| 5-F | cyclohexyl | 163.5–164.5 | 63 |
| 4-Cl | cyclohexyl | 173–174 | 69 |
| 5-CF₃ | cyclohexyl | 177.5–178.5d | 40 |
| 6-F | cyclohexyl | 203–206 | 43 |
| H | t-butyl | 151–152 | 35 |
| 5-CH₃ | t-butyl | 202.5d | 34 |
| 5-Cl | t-butyl | 176.5–177.5d | 43 |
| 5-F | t-butyl | 161.5–162.5d | 31 |
| 6-Cl | t-butyl | 146–147 | 42 |
| H | isopropyl | 114–115 | 23 |
| 5-CH₃ | isopropyl | 169–171 | 38 |
| 5-Cl | isopropyl | 164–165 | 77 |
| 6-Cl | isopropyl | 128–129 | 69 |
| H | phenoxymethyl | 187–188 | 78 |
| 5-Cl | phenoxymethyl | 218–219 | 51 |

[1]The letter "d" in this column indicates that the material melted with decomposition.

EXAMPLE 16

By reaction of the appropriate 2-oxindole with the requisite acyl isocyanate, substantially according to the procedure of Example 14, the following compounds can be prepared:

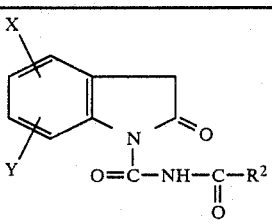

| X | Y | R² |
|---|---|---|
| H | H | 3-butoxyphenyl |
| 5-Br | H | 4-isobutylphenyl |
| H | 5-Br | methyl |
| n-C₄H₉ | H | ethyl |
| H | 5-C₂H₅O | hexyl |
| 6-n-C₄H₉O | H | cyclopropyl |

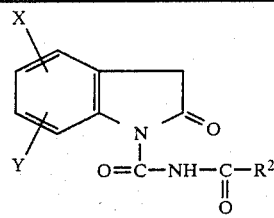

| X | Y | R² |
|---|---|---|
| H | 5-n-C₄H₉O | cyclopentyl |
| 5-CH₃O | 6-CH₃O | cyclohexyl |
| 7-Cl | H | propyl |
| 4-CH₃S | H | phenyl |
| 5-n-C₄H₉S | H | 3-fluorophenyl |
| H | H | cycloheptyl |
| 5-Cl | H | butyl |
| H | H | 4-ethylphenyl |
| 4-Cl | H | phenyl |
| 6-Cl | H | cyclobutyl |
| 6-Cl | H | pentyl |
| 5-F | H | 4-chlorophenyl |
| 6-Cl | H | 4-methoxyphenyl |
| 5-CH₃ | H | hexyl |
| H | H | 3,4-dichlorophenyl |
| 4-CH₃ | 5-CH₃ | cyclohexyl |
| 5-Cl | H | 3,4-diethoxyphenyl |
| 5-CH₃ | 6-CH₃ | phenyl |
| 5-F | H | 3-fluoro-4-chlorophenyl |
| 5-OCH₃ | H | cyclobutyl |
| 5-CF₃ | H | 2,4-difluorophenyl |
| 6-Cl | H | 3,5-dichlorophenyl |
| 6-Br | H | ethyl |
| H | H | 3-ethoxy-4-butoxyphenyl |
| 5-Cl | 6-Cl | 4-methoxyphenyl |
| 6-F | H | cyclohexyl |
| 5-F | 6-Cl | 2,4-dimethylphenyl |
| 6-CF₃ | H | 4-chlorophenyl |
| 5-CH₃ | 6-F | 3,5-dimethylphenyl |
| 6-OCH₃ | H | cycloheptyl |
| H | H | 4-trifluoromethylphenyl |
| 5-CH₃SO | H | phenyl |
| 5-n-C₄H₉SO | H | cyclohexyl |
| 4-CH₃SO₂ | H | phenoxymethyl |
| 5-n-C₄H₉SO₂ | H | phenyl |
| 5-NO₂ | H | cyclohexyl |
| 6-C₆H₅ | H | 2-furyl |
| H | 5-Br | cyclohexyl |
| 5-CH₃CO | H | phenyl |
| 6-n-C₃H₇CO | H | n-hexyl |
| 5-Cl | H | 3-thienyl |
| 5-C₆H₅CO | H | cyclohexyl |
| 5-C₄H₃SCO[1] | H | 3-methylphenyl |
| 5-CH₃CONH | H | ethyl |
| 5-(CH₃)₂CHCONH | H | phenyl |
| 5-C₆H₅CONH | H | phenyl |
| 5-CH₃ | 6-CH₃ | 3-pyridyl |
| 5-SO₂N(CH₃)₂ | H | phenyl |
| 5-F | 6-F | 2-methylphenyl |
| 5-SO₂N(n-C₃H₇)₂ | H | n-hexyl |

[1]5-(2-thenoyl)

EXAMPLE 17

By reaction of 5,6-methylenedioxy-2-oxindole with benzoyl isocyanate, 5,6-ethylenedioxy-2-oxindole with cyclohexylcarbonyl isocyanate, 5-cyclopropyl-2-oxindole with benzoyl isocyanate and 5-cycloheptyl-2-oxindole with isobutyryl isocyanate, the following compounds can be prepared:
N-benzoyl-5,6-methylenedioxy-2-oxindole-1-carboxamide,
N-cyclohexylcarbonyl-5,6-ethylenedioxy-2-oxindole-1-carboxamide,
N-benzoyl-5-cyclopropyl-2-oxindole-1-carboxamide and N-isobutyryl-5-cycloheptyl-2-oxindole-1-carboxamide, respectively.

EXAMPLE 18

The N-substituted-2-oxindole-1-carboxamides in the table below can be prepared by reaction of the corresponding 2-oxindole compound with the requisite acyl isocyanate.

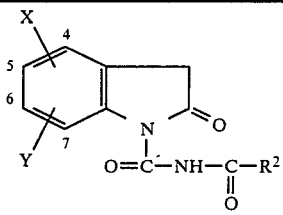

| X and Y* | R² |
|---|---|
| 4-CH₂—CH₂—CH₂—5 | phenyl |
| 5-CH₂—CH₂—CH₂—6 | cyclohexyl |
| 6-CH₂—CH₂—CH₂—CH₂—7 | 4-fluorophenyl |
| 5-CH=CH—CH=CH—6 | t-butyl |
| 5-O—CH₂—CH₂—6 | isopropyl |
| 5-CH₂—CH₂—O—6 | phenyl |
| 5-S—CH₂—CH₂—6 | cyclohexyl |
| 5-O—CH=CH—6 | t-butyl |
| 5-S—CH=CH—6 | cyclohexyl |
| 5-CH=CH—S—6 | phenyl |

*In this column, the numeral to the left of the formula indicates the point attachment of that end of the formula to the 2-oxindole nucleus and the numeral to the right indicates the point of attachment of that end of the formula to the 2-oxindole nucleus.

PREPARATION 1

3-(2-Furoyl)-2-oxindole

To a stirred solution of 5.5 g (0.24 mole) of sodium in 150 ml of ethanol was added 13.3 g (0.10 mole) of 2-oxindole at room temperature. The resulting slurry was cooled to ice-bath temperature, and then 15.7 g (0.12 mole) of 2-furoyl chloride was added, dropwise, during 10-15 minutes. The ice-bath was removed, and additional 100 ml of ethanol was added and then the reaction mixture was heated under reflux for 7 hours. The reaction mixture was allowed to stand overnight and then the solid was filtered off. The solid was added to 400 ml of water and the resulting mixture was acidified using concentrated hydrochloric acid. The mixture was cooled with ice and the solid was collected by filtration. The solid residue was recrystallized from 150 ml of acetic acid, affording 8.3 g of yellow crystals, mp 209-210 (dec).

Analysis: Calcd. for $C_{13}H_9O_3N$: C, 68.72; H, 3.99; N, 6.17%. Found: C, 68.25; H, 4.05; N, 6.20%.

PREPARATION 2

Reaction of 2-oxindole with the appropriate acid chloride gave the following additional products:
3-(2-thenoyl)-2-oxindole, mp 189°-190° C., 17% yield;
3-(2-[2-thienyl]acetyl)-2-oxindole, mp 191°-192.5° C., 38% yield; and
3-(2-phenoxyacetyl)-2-oxindole, mp 135°-136° C., 42% yield.

PREPARATION 3

3-(3-Furoyl)-2-oxindole

To a stirred solution of 2.8 g (0.12 mole) of sodium in 200 ml of ethanol was added 13.3 g (0.10 mole) of 2-oxindole, followed by 16.8 g of ethyl 3-furoate. The mixture was heated under reflux for 47 hours, cooled and then the solvent was removed by evaporation in vacuo. The residue was triturated under 200 ml of ether, and the solid was collected by filtration and discarded. The filtrate was evaporated in vacuo, and the residue triturated under diisopropyl ether and recovered by filtration. The solid was suspended in 250 ml of water, which was then acidified with concentrated hydrochloric acid. This mixture was stirred to give a solid, which was recovered by filtration. This latter solid was recrystallized from acetic acid followed by acetonitrile to give 705 mg of the title compound, mp 185°-186° C.

Analysis: Calcd. for $C_{13}H_9O_3N$: C, 68.72; H, 3.99; N, 6.17%. Found: C, 68.72; H, 4.14; N, 6.14%.

PREPARATION 4

5-Chloro-2-oxindole

To a stirred slurry of 100 g (0.55 mol) of 5-chloroisatin in 930 ml of ethanol was added 40 ml (0.826 mol) of hydrazine hydrate, resulting in a red solution. The solution was heated under reflux for 3.5 hours, during which time a precipitate appeared. The reaction mixture was stirred overnight, and then the precipitate was recovered by filtration to give 5-chloro-3-hydrazono-2-oxindole as a yellow solid, which was dried in a vacuum oven. The dried solid weighed 105.4 g.

The dried solid was then added portionwise, during 10 minutes, to a solution of 125.1 g of sodium methoxide in 900 ml of absolute ethanol. The resultant solution was heated under reflux for 10 minutes and then it was concentrated in vacuo to a gummy solid. The gummy solid was dissolved in 400 ml of water and the aqueous solution thus obtained was decolorized with activated carbon and then poured into a mixture of 1 liter of water and 180 ml of concentrated hydrochloric acid containing ice chips. A tan solid precipitated and it was collected by filtration and washed thoroughly with water. The solid was dried and then it was washed with diethyl ether. Finally it was recrystallized from ethanol to give 48.9 g of the title compound, mp 193°-195° C. (dec).

In an analogous fashion, 5-methylisatin was converted into 5-methyl-2-oxindole by treatment with hydrazine hydrate followed sodium ethoxide in ethanol. The product melted at 173°-174° C.

PREPARATION 5

4,5-Dimethyl-2-oxindole and 5,6-dimethyl-2-oxindole 3,4-Dimethylaniline was converted into 3,4-dimethyl-isonitrosoacetanilide by reaction with chloral hydrate and hydroxylamine, using the method described in "Organic Syntheses," Collective Volume I, page 327. The 3,4-dimethyl-isonitrosoacetanilide was cyclized with sulfuric acid, according to the method of Baker et al., *Journal of Organic Chemistry*, 17, 149 (1952), to give 4,5-dimethylisatin (m.p. 225°-226° C.) and 5,6-dimethylisatin (m.p. 217°-218° C.).

4,5-Dimethylisatin was converted into 4,5-dimethyl-2-oxindole, m.p. 245.5°-247.5° C., by treatment with hydrazine hydrate, followed by sodium ethoxide in ethanol, substantially according to the procedure of Preparation 4.

In like manner, 5,6-dimethylisatin was converted into 5,6-dimethyl-2-oxindole, m.p. 196.5°-198° C., by treatment with hydrazine hydrate, followed by sodium ethoxide in ethanol, substantially according to the procedure of Preparation 4.

PREPARATION 6

4-Chloro-2-oxindole and 6-chloro-2-oxindole

A. 3-Chloro-isonitrosoacetanilide

To a stirred solution of 113.23 g (0.686 mol) of chloral hydrate in 2 liters of water was added 419 g (2.95 mol) of sodium sulfate, followed by a solution prepared from 89.25 g (0.70 mol) of 3-chloroaniline, 62 ml of concentrated hydrochloric acid and 500 ml of water. A thick precipitate formed. To the reaction mixture was then added, with stirring, a solution of 155 g (2.23 mol) of hydroxylamine in 500 ml of water. Stirring was continued and the reaction mixture was warmed slowly and it was maintained between 60 and 75° C. for approximately 6 hours, during which time an additional 1 liter of water had been added to facilitate stirring. The reaction mixture was then cooled and the precipitate was recovered by filtration. The wet solid was dried to give 136.1 g of 3-chloroisonitrosoacetanilide.

B. 4-Chloroisatin and 6-chloroisatin

To 775 ml of concentrated sulfuric acid, preheated to 70° C., was added, with stirring, 136 g of 3-chloroisonitrosoacetanilide at such a rate as to maintain the reaction medium at a temperature between 75° and 85° C. When all the solid had been added, the reaction mixture was heated at 90° C. for an additional 30 minutes. The reaction mixture was then cooled, and poured slowly onto ca 2 liters of ice, with stirring. Additional ice was added as necessary to maintain the temperature below room temperature. A red-orange precipitate formed which was recovered by filtration, washed with water and dried. The resultant solid was slurried in 2 liters of water, and then it was brought into solution by the addition of ca 700 ml of 3N sodium hydroxide. The solution was filtered, and then pH was adjusted to 8 with concentrated hydrochloric acid. At this point, 120 ml of a mixture of 80 parts water and 20 parts concentrated hydrochloric acid was added. The solid which precipitated was recovered by filtration, washed with water and dried to give 50 g of crude 4-chloroisatin. The filtrate from which the 4-chloroisatin had been recovered was further acidified to pH 0 using concentrated hydrochloric acid, whereupon a further precipitate formed. It was recovered by filtration, washed with water and dried, to give 43 g of crude 6-chloroisatin.

The crude 4-chloroisatin was recrystallized from acetic acid to give 43.3 g of material melting at 258°–259° C.

The crude 6-chloroisatin was recrystallized from acetic acid to give 36.2 g of material melting at 261°–262° C.

C. 4-Chloro-2-oxindole

To a stirred slurry of 43.3 g of 4-chloroisatin in 350 ml of ethanol was added 17.3 ml of hydrazine hydrate, and then the reaction mixture was heated under reflux for 2 hours. The reaction mixture was cooled, and the precipitate was recovered by filtration to give 43.5 g of 4-chloro-3-hydrazono-2-oxindole, mp 235°–236° C.

To a stirred solution of 22 g of sodium in 450 ml of anhydrous ethanol was added, portionwise, 43.5 g of 4-chloro-3-hydrazono-2-oxindole, and the resulting solution was heated under reflux for 30 minutes. The cooled solution was then concentrated to a gum, which was dissolved in 400 ml of water and decolorized using activated carbon. The resulting solution was poured onto a mixture of 1 liter of water and 45 ml of concentrated hydrochloric acid. The precipitate which formed was recovered by filtration, dried and recrystallized from ethanol, giving 22.4 g of 4-chloro-2-oxindole, mp 216°–218° C. (dec).

D. 6-Chloro-2-oxindole

Reaction of 36.2 g of 6-chloroisatin with hydrazine hydrate followed by sodium ethoxide in ethanol, substantially according to C above, afforded 14.2 g of 6-chloro-2-oxindole, mp 196°–198° C.

PREPARATION 7

5,6-Difluoro-2-oxindole

Reaction of 3,4-difluoroaniline with chloral hydrate and hydroxylamine followed cyclization with sulfuric acid, in a manner analogous to Parts A and B of Preparation 6, gave 5,6-difluoroisatin, which was reacted with hydrazine hydrate followed by sodium methoxide in ethanol, in a manner analogous to Preparation 4, to give the title compound, m.p. 187°–190° C.

PREPARATION 8

5-Fluoro-2-oxindole

To a stirred solution of 11.1 g (0.1 mol) of 4-fluoroaniline in 200 ml of dichloromethane, at −60° to −65° C., was added, dropwise, a solution of 10.8 g (0.1 mol) of t-butyl hypochlorite in 25 ml of dichloromethane. Stirring was continued for 10 minutes at −60° to −65° C., and then was added, dropwise, a solution of 13.4 g (0.1 mol) of ethyl 2-(methylthio)acetate in 25 ml of dichloromethane. Stirring was continued at −60° C. for 1 hour and then was added, dropwise, at −60° to −65° C., a solution of 11.1 g (0.11 mol) of triethylamine in 25 ml of dichloromethane. The cooling bath was removed, and when the reaction mixture had warmed to room temperature, 100 ml of water was added. The phases were separated, and the organic phase was washed with saturated sodium chloride solution, dried ($Na_2SO_4$) and evaporated in vacuo. The residue was dissolved in 350 ml of diethyl ether, to which was added 40 ml of 2N hydrochloric acid. This mixture was stirred at room temperature overnight. The phases were separated and the ether phase was washed with water, followed saturated sodium chloride. The dried ($Na_2SO_4$) ether phase was evaporated in vacuo to give 17 g of an orange-brown solid which was triturated under isopropyl ether. The solid was then recrystallized form ethanol, to give 5.58 g of 5-fluoro-3-methylthio-2-oxindole, mp 151.5°–152.5° C.

Analysis: Calcd for $C_9H_8ONFS$: C, 54.80; H, 4.09; N, 7.10%. Found: C, 54.74; H, 4.11; N, 7.11%.

A sample of the above 5-fluoro-3-methylthio-2-oxindole (986 mg, 5.0 mmol) was added to 2 teaspoonsful of Raney nickel under 50 ml of absolute ethanol, and then the reaction mixture was heated under reflux for 2 hours. The catalyst was removed by decantation and was washed with absolute ethanol. The combined ethanol solutions were evaporated in vacuo and the residue was dissolved in dichloromethane. The dichloromethane solution was dried ($Na_2SO_4$) and evaporated in vacuo to give 475 mg of 5-fluoro-2-oxindole, mp 121°–134° C.

In analogous fashion, 4-trifluoromethylaniline was reacted with t-butyl hypochlorite, ethyl 2-(methylthio)acetate and triethylamine followed by reduction of the 3-thiomethyl-5-trifluoromethyl-2-oxindole thus obtained with Raney nickel, to give 5-trifluoromethyl-2-oxindole, mp 189.5°–190.5° C.

PREPARATION 9

5-Methoxy-2-oxindole

5-Methoxy-2-oxindole was prepared from 4-methoxyaniline in a manner similar to the procedure of Preparation 8, except that the initial chlorination step was carried out using a solution of chlorine gas in dichloromethane in place of t-butyl hypochlorite. Th title product melted at 150.5°–151.5° C.

PREPARATION 10

6-Chloro-5-fluoro-2-oxindole

To 130 ml of toluene was added, with stirring, 24.0 g (0.165 mole) of 3-chloro-4-fluoroaniline and 13.5 ml (0.166 mole) of pyridine. The resulting solution was cooled to ca 0° C. and 13.2 ml (0.166 mole) of 2-chloroacetyl chloride was added. The reaction mixture was stirred at room temperature for 5 hours and then it was extracted twice with 100 ml of 1N hydrochloric acid, followed by 100 ml of saturated sodium chloride solution. The resulting toluene solution was dried using magnesium sulfate, and then it was concentrated in vacuo to give 32.6 g (88% yield) of N-(2-chloroacetyl)-3-chloro-4-fluoroaniline.

A 26.63-g sample of the N-(2-chloroacetyl)-3-chloro-4-fluoroaniline was thoroughly mixed with 64 g of anhydrous aluminum chloride, and the mixture was heated at 210°–230° C. for 8.5 hours. The reaction mixture was then poured onto a mixture of ice and 1N hydrochloric acid, with stirring. Stirring was continued for 30 minutes, and then the solid was collected by filtration (22.0 g). The solid was dissolved in 1:1 ethyl acetate-hexane and chromatographed on 800 g of silica gel. Elution of the column, followed by evaporation of the fractions, produced 11.7 g of the N-(2-chloroacetyl)-3-chloro-4-fluoroaniline, followed by 3.0 g of 6-chloro-5-fluoro-2-oxindole. The latter material was recrystallized from toluene to give 1.70 g (7% yield) of the title compound, mp 196°–206° C. Analysis by NMR spectroscopy indicated that the product was contaminated by some 4-chloro-5-fluoro-2-oxindole. A second crop weighing 0.8 g was obtained.

PREPARATION 11

6-Fluoro-5-methyl-2-oxindole

An intimate mixture of 11.62 g (57.6 mmol) of N-(2-chloroacetyl)-3-fluoro-4-methylaniline and 30.6 g (229.5 mmol) of anhydrous aluminum chloride was heated to 210°–220° C. After 4 hours, the reaction mixture was cooled and then added to 100 ml of 1N hydrochloric acid and 50 ml of ice. A tan solid formed, which was collected by filtration and recrystallized from aqueous ethanol. Three crops were obtained, weighing 4.49 g, 2.28 g and 1.0 g, respectively. The crop weighing 1.0 g was further recrystallized from water to give 280 mg of the title compound, mp 168.5°–171° C.

PREPARATION 12

6-Bromo-2-oxindole

To 9.4 g of sodium hydride was added 195 ml of dimethyl sulfoxide, followed by the dropwise addition of 22.37 ml of dimethyl malonate. At the end of the addition, the mixture was heated to 100° C. and maintained at that temperature for 40 minutes. At this point, 25 g of 1,4-dibromo-2-nitrobenzene was added all at once. The reaction mixture was maintained at 100° C. for 4 hours and then it was added to 1.0 liter of saturated ammonium chloride solution. The resulting mixture was extracted with ethyl acetate and the extracts were washed with ammonium chloride solution, water and saturated sodium chloride. The dried (MgSO$_4$) solution was evaporated, and the residue was recrystallized from ethyl acetate-hexane to give 22.45 g of dimethyl 2-(4-bromo-2-nitrophenyl)malonate.

A solution of 17.4 g of dimethyl 2-(4-bromo-2nitrophenyl)malonate and 4.6 g of lithium chloride in 150 ml of dimethyl sulfoxide was placed in an oil bath at 100° C. After 3 hours, the reaction mixture was cooled to room temperature and then it was poured into a mixture of 500 ml of ethyl acetate and 500 ml of saturated sodium chloride solution. The layers were separated and the aqueous layer was extracted with further ethyl acetate. The combined organic layers were washed with saturated sodium chloride solution, dried using sodium sulfate, and then evaporated in vacuo. The residue was chromatographed using silica gel as adsorbant and ethyl acetate-hexane mixture as eluant. This afforded 9.4 g of methyl 2-(4-bromo-2-nitrophenyl)acetate.

To a solution of 7.4 g of methyl 2-(4-bromo-2nitrophenyl)acetate in 75 ml of acetic acid was added 6.1 g of iron powder. The reaction mixture was placed in an oil bath at 100° C. After 1 hour, the solvent was removed by evaporation in vacuo, and the residue was dissolved in 250 ml of ethyl acetate. The solution was filtered, washed with saturated sodium chloride solution, dried using sodium sulfate, decolorized using activated carbon, and evaporated in vacuo. This afforded 5.3 g of 6-bromo-2-oxindole as a white crystalline solid, m.p. 213°–214° C.

In like manner, starting with 1,4,5-trichloro-2-nitrobenzene, 5,6-dichloro-2-oxindole was prepared, m.p. 209°–210° C.

PREPARATION 13

6-Phenyl-2-oxindole

To 3.46 g. (0.072 mole) of sodium hydride was added 50 ml. of dimethyl sulfoxide followed by the dropwise addition of a solution of 8.2 ml. (0.072 mole) of dimethyl malonate in 10 ml. of dimethyl sulfoxide, with stirring. After completion of the addition, stirring was continued for 1 hour, and then a solution of 10 g. (0.036 mole) of 4-bromo-3-nitrodiphenyl in 50 ml. of dimethyl sulfoxide was added. The reaction mixture was heated to 100° C. for 1 hour, cooled, and poured onto a mixture of ice-water containing 5 g. of ammonium chloride. The mixture thus obtained was extracted with ethyl acetate, and the extracts were washed with sodium chloride solution and dried using magnesium sulfate. Evaporation in vacuo to give an oil, which was chromatographed using silica gel and then recrystallized from methanol to afford 6 g. of dimethyl 2-(3-nitro-4-diphenylyl)malonate, m.p. 82°–83° C.

A portion (5 g.) of the above nitro compound was reduced with hydrogen over a platinum catalyst, in a mixture of 50 ml. of tetrahydrofuran and 10 ml. of methanol, at a pressure of ca 5 kg/cm$^2$, to give the corresponding amine. The latter compound was refluxed in ethanol for 16 hours, and then the product was recovered by solvent evaporation and recrystallized from methanol to give 1.1 g. of ethyl 6-phenyl-2-oxindole-1-carboxylate, m.p. 115°–117° C.

The above ethyl ester (1.0 g.) and 100 ml. of 6N hydrochloric acid was heated under reflux for 3 hours and then allowed to stand at room temperature for 3 days.

The solid was collected by filtration and dried, to give 700 mg. of 6-phenyl-2-oxindole, m.p. 175°–176° C.

PREPARATION 14

5-Acetyl-2-oxindole

To 95 ml. of carbon disulfide was added 27 g. (0.202 mole) of aluminum chloride, followed by the dropwise addition of a solution of 3 ml. (0.042 mole) of acetyl chloride in 5 ml. of carbon disulfide, with stirring. Stirring was continued for 5 minutes and then 4.4 g. (0.033 mole) of 2-oxindole was added. The resulting mixture was heated under reflux for 4 hours and cooled. The carbon disulfide was removed by decantation and the residue was triturated under water and recovered by filtration. After drying, 3.2 g. of the title compound was obtained, m.p. 225°–227° C.

Reaction of 2-oxindole with benzoyl chloride and with 2-thenoyl chloride in the presence of aluminum chloride, substantially according to the above procedure, afforded the following compounds:

5-benzoyl-2-oxindole, m.p. 203°–205° C. (from $CH_3OH$) and 5-(2-thenoyl)-2-oxindole, m.p. 211°–213° C. (from $CH_3CN$).

PREPARATION 15

5-Bromo-2-oxindole, 5-nitro-2-oxindole and 5-amino-2-oxindole can be prepared as described in Beckett et al., *Tetrahedron*, 24, 6093 (1968). 5-Amino-2-oxindole can be acylated to give 5-alkanamido-2-oxindole and 5-benzamido-2-oxindole, using standard procedures.

5-n-Butyl-2-oxindole can be prepared by reaction of 5-n-butylisatin with hydrazine hydrate followed by sodium methoxide in ethanol, according to the procedure of Preparation 4. 5-n-Butylisatin can be prepared from 4-n-butylaniline by treatment with chloral hydrate and hydroxylamine, followed by cyclization with sulfuric acid, according to the procedure of Parts A and B of Preparation 6.

5-Ethoxy-2-oxindole can be prepared by conversion of 3-hydroxy-6-nitro-toluene into 3-ethoxy-6-nitrotoluene by standard methods (potassium carbonate and ethyl iodide in acetone), followed by conversion of the 3-ethoxy-6-nitrotoluene into 5-ethoxy-2-oxindole by the method described by Beckett et al., (*Tetrahedron*, 24, [1968]), for the conversion of 3-methoxy-6-nitrotoluene into 5-methoxy-2-oxindole. 5-n-Butoxy-2-oxindole can be prepared in like manner, but substituting n-butyl iodide for ethyl iodide.

5,6-Dimethoxy-2-oxindole can be prepared by the method of Walker, *Journal of the American Chemical Society*, 77, 3844 (1955).

7-Chloro-2-oxindole can be prepared by the method described in U.S. Pat. No. 3,882,236.

4-Thiomethyl-2-oxindole and 6-thiomethyl-2-oxindole can be prepared by the method described in U.S. Pat. No. 4,006,161. 5-n-Butylthio-2-oxindole can be prepared in like manner, but substitituted 4-butylthioaniline for the 3-methylthioaniline.

5,6-Methylenedioxy-2-oxindole can be prepared by the method of McEvoy et al., *Journal of Organic Chemistry*, 38, 3350 (1973). 5,6-Ethylenedioxy-2-oxindole can be prepared in analogous fashion.

6-Fluoro-2-oxindole can be prepared according to Protiva et al., *Collection of Czechoslovakian Chemical Communications*, 44, 2108 (1979) and U.S. Pat. No. 4,160,032.

6-Trifluoromethyl-2-oxindole can be prepared according to Simet, *Journal of Organic Chemistry*, 28, 3580 (1963).

6-Methoxy-2-oxindole can be prepared according to Wieland et al., *Chemische Berichte*, 96, 253 (1963).

5-Cyclopropyl-2-oxindole and 5-cycloheptyl-2-oxindole can be prepared by reaction of 5-cyclopropylisatin and 5-cycloheptylisatin, respectively, with hydrazine hydrate followed by sodium methoxide in ethanol, according to the procedure of Preparation 4. 5-Cyclopropylisatin and 5-cycloheptylisatin can be prepared from 4-cyclopropylaniline and 4-cycloheptylaniline, respectively, by treatment with chloral hydrate and hydroxylamine, followed by cyclization with sulfuric acid, according to Parts A and B of Preparation 6.

I claim:

1. A 2-oxindole compound of the formula

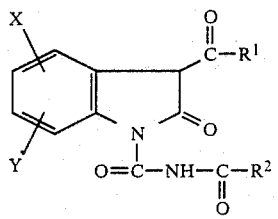

and the pharmaceutically-acceptable base salts thereof; wherein

X is selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons, trifluoromethyl, alkylsulfinyl having 1 to 4 carbons, alkylsulfonyl having 1 to 4 carbons, nitro, phenyl, alkanoyl having 2 to 4 carbons, benzoyl, thenoyl, alkanamido having 2 to 4 carbons, benzamido and N,N-dialkylsulfamoyl having 1 to 3 carbons in each of said alkyls; and Y is selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons and trifluoromethyl;

or X and Y when taken together are a 4,5-, 5,6- or 6,7-methylenedioxy group or a 4,5-, 5,6- or 6,7-ethylenedioxy group;

or X and Y when taken together and when attached to adjacent carbon atoms, form a divalent radical Z, wherein Z is selected from the group consisting of

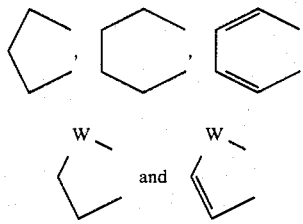

wherein W is oxygen or sulfur;

$R^1$ is selected from the group consisting of alkyl having 1 to 6 carbons, cycloalkyl having 3 to 7 carbons, phenyl, substituted phenyl, phenylalkyl having 1 to 3 carbons in said alkyl, (substituted phenyl)alkyl having 1 to 3 carbons in said alkyl, phenoxyalkyl having 1 to 3 carbons in said alkyl, (substituted phenoxy)alkyl having 1 to 3 carbons in said alkyl, naphthyl and —(CH$_2$)$_n$—Q—R°;

wherein the substituent on said substituted phenyl, said (substituted phenyl)alkyl and said (substituted phenoxy)alkyl is selected from the group consisting of fluoro, chloro, alkyl having 1 to 3 carbons, alkoxy having 1 to 3 carbons and trifluoromethyl; n is zero, 1 or 2; Q is a divalent radical derived from a compound selected from the group consisting of furan, thiophene, pyrrole, thiazole, isothiazole, oxazole, isoxazole, 1,2,3-thiadiazole, 1,2,5-thiadiazole, tetrahydrofuran, tetrahydrothiophene, pyridine, pyrimidine, pyrazine, benzo[b]furan and benzo[b]thiophene; and R° is hydrogen or alkyl having 1 to 3 carbons;

and R$^2$ is selected from the group consisting of alkyl having 1 to 6 carbons, cycloalkyl having 3 to 7 carbons, phenoxymethyl, furyl, thienyl, pyridyl and

wherein R$^3$ and R$^4$ are each selected from the group consisting of hydrogen, fluoro, chloro, alkyl having 1 to 4 carbons, alkoxy having 1 to 4 carbons and trifluoromethyl.

2. A compound according to claim 1, wherein
X and Y are each selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons and trifluoromethyl;
or X and Y when taken together are a 4,5-, 5,6- or 6,7-methylenedioxy group or a 4,5-, 5,6- or 6,7-ethylenedioxy group;
R$^1$ is selected from the group consisting of alkyl having 1 to 6 carbons, cycloalkyl having 3 to 7 carbons, phenyl, phenylalkyl having 1 to 3 carbons in said alkyl, phenoxyalkyl having 1 to 3 carbons in said alkyl, furyl, thienyl, pyrrolyl, alkylfuryl having 1 to 3 carbons in said alkyl, alkylthienyl having 1 to 3 carbons in said alkyl, furylalkyl having 1 to 3 carbons in said alkyl, thienylalkyl having 1 to 3 carbons in said alkyl, naphthyl, benzo[b]furyl and benzo[b]thienyl;
and R$^2$ is selected from the group consisting of alkyl having 1 to 6 carbons, cycloalkyl having 3 to 7 carbons, phenoxymethyl and

wherein R$^3$ and R$^4$ are each selected from the group consisting of hydrogen, fluoro, chloro, alkyl having 1 to 4 carbons, alkoxy having 1 to 4 carbons and trifluoromethyl.

3. A compound according to claim 2, wherein Y is hydrogen.

4. A compound according to claim 3, wherein X is hydrogen.

5. A compound according to claim 4, wherein R$^1$ is selected from the group consisting of furyl, thienyl and said thienylalkyl.

6. A compound according to claim 4, wherein R$^1$ is selected from 2-furyl, 2-thienyl and (2-thienyl)methyl.

7. A compound according to claim 6, wherein R$^2$ is t-butyl.

8. The compound according to claim 7, wherein R$^1$ is (2-thienyl)methyl.

9. A compound according to claim 6, wherein R$^2$ is cyclohexyl.

10. The compound according to claim 9, wherein R$^1$ is (2-thienyl)methyl.

11. A compound according to claim 6, wherein R$^2$ is phenyl.

12. The compound according to claim 11, wherein R$^1$ is 2-furyl.

13. A compound according to claim 3, wherein X is 5-chloro.

14. A compound according to claim 13, wherein R$^1$ is selected from 2-furyl, 2-thienyl and (2-thienyl)methyl.

15. A compound according to claim 14, wherein R$^2$ is cyclohexyl.

16. The compound according to claim 15, wherein R$^1$ is 2-thienyl.

17. A method of eliciting an analgesic response in a mammalian subject, which comprises administering to said mammalian subject an analgesic response eliciting amount of a 2-oxindole compound of the formula

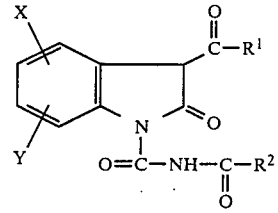

or a pharmaceutically-acceptable base salt thereof; wherein
X is selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons, trifluoromethyl, alkylsulfinyl having 1 to 4 carbons, alkylsulfonyl having 1 to 4 carbons, nitro, phenyl, alkanoyl having 2 to 4 carbons, benzoyl, thenoyl, alkanamido having 2 to 4 carbons, benzamido and N,N-dialkylsulfamoyl having 1 to 3 carbons in each of said alkyls; and Y is selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons and trifluoromethyl;
or X and Y when taken together are a 4,5-, 5,6- or 6,7-methylenedioxy group or a 4,5-, 5,6- or 6,7-ethylenedioxy group;
or X and Y when taken together and when attached to adjacent carbon atoms, form a divalent radical Z, wherein Z is selected from the group consisting of

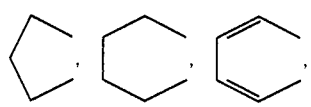

-continued

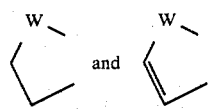

wherein W is oxygen or sulfur;

R¹ is selected from the group consisting of alkyl having 1 to 6 carbons, cycloalkyl having 3 to 7 carbons, phenyl, substituted phenyl, phenylalkyl having 1 to 3 carbons in said alkyl, (substituted phenyl)alkyl having 1 to 3 carbons in said alkyl, phenoxyalkyl having 1 to 3 carbons in said alkyl, (substituted phenoxy)alkyl having 1 to 3 carbons in said alkyl, naphthyl and —(CH$_2$)$_n$—Q—R°;

wherein the substituent on said substituted phenyl, said (substituted phenyl)alkyl and said (substituted phenoxy)alkyl is selected from the group consisting of fluoro, chloro, alkyl having 1 to 3 carbons, alkoxy having 1 to 3 carbons and trifluoromethyl; n is zero, 1 or 2; Q is a divalent radical derived from a compound selected from the group consisting of furan, thiophene, pyrrole, thiazole, isothiazole, oxazole, isoxazole, 1,2,3-thiadiazole, 1,2,5-thiadiazole, tetrahydrofuran, tetrahydrothiophene, pyridine, pyrimidine, pyrazine, benzo[b]furan and benzo[b]thiophene; and R° is hydrogen or alkyl having 1 to 3 carbons;

and R² is selected from the group consisting of alkyl having 1 to 6 carbons, cycloalkyl having 3 to 7 carbons, phenoxymethyl, furyl, thienyl, pyridyl and

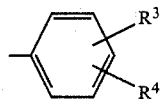

wherein R³ and R⁴ are each selected from the group consisting of hydrogen, fluoro, chloro, alkyl having 1 to 4 carbons, alkoxy having 1 to 4 carbons and trifluoromethyl.

18. The method according to claim 17, wherein

X and Y are each selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons and trifluoromethyl;

or X and Y when taken together are a 4,5-, 5,6- or 6,7-methylenedioxy group or a 4,5-, 5,6- or 6,7-ethylenedioxy group;

R¹ is selected from the group consisting of alkyl having 1 to 6 carbons, cycloalkyl having 3 to 7 carbons, phenyl, phenylalkyl having 1 to 3 carbons in said alkyl, phenoxyalkyl having 1 to 3 carbons in said alkyl, furyl, thienyl, pyrrolyl, alkylfuryl having 1 to 3 carbons in said alkyl, alkylthienyl having 1 to 3 carbons in said alkyl, furylalkyl having 1 to 3 carbons in said alkyl, thienylalkyl having 1 to 3 carbons in said alkyl, naphthyl, benzo[b]furyl and benzo[b]thienyl;

and R² is selected from the group consisting of alkyl having 1 to 6 carbons, cycloalkyl having 3 to 7 carbons, phenoxymethyl and

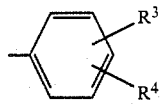

wherein R³ and R⁴ are each selected from the group consisting of hydrogen, fluoro, chloro, alkyl having 1 to 4 carbons, alkoxy having 1 to 4 carbons and trifluoromethyl.

19. The method according to claim 18, wherein X and Y are both hydrogen.

20. The method according to claim 19, wherein R¹ is selected from the group consisting of 2-furyl, 2-thienyl and (2-thienyl)methyl.

21. The method according to claim 20, wherein R² is phenyl.

22. The method according to claim 21, wherein R¹ is 2-furyl.

23. The method according to claim 18, wherein X is 5-chloro and Y is hydrogen.

24. The method according to claim 23, wherein R¹ is selected from 2-furyl, 2-thienyl and (2-thienyl)methyl.

25. The method according to claim 24, wherein R² is cyclohexyl.

26. The method according to claim 25, wherein R¹ is 2-thienyl.

27. A method of treating an inflammatory disease in a mammalian subject, which comprises administering to said mammalian subject an inflammatory disease treating amount of a 2-oxindole compound of the formula

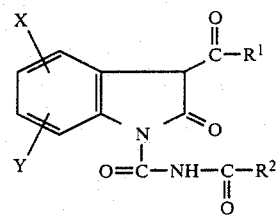

or a pharmaceutically-acceptable base salt thereof; wherein

X is selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons, trifluoromethyl, alkylsulfinyl having 1 to 4 carbons, alkylsulfonyl having 1 to 4 carbons, nitro, phenyl, alkanoyl having 2 to 4 carbons, benzoyl, thenoyl, alkanamido having 2 to 4 carbons, benzamido and N,N-dialkylsulfamoyl having 1 to 3 carbons in each of said alkyls; and Y is selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons and trifluoromethyl;

or X and Y when taken together are a 4,5-, 5,6- or 6,7-methylenedioxy group or a 4,5-, 5,6- or 6,7-ethylenedioxy group;

or X and Y when taken together and when attached to adjacent carbon atoms, form a divalent radical Z, wherein Z is selected from the group consisting of

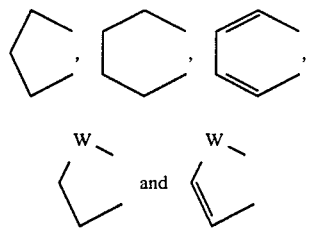

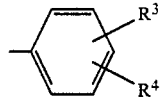

wherein W is oxygen or sulfur;

R[1] is selected from the group consisting of alkyl having 1 to 6 carbons, cycloalkyl having 3 to 7 carbons, phenyl, substituted phenyl, phenylalkyl having 1 to 3 carbons in said alkyl, (substituted phenyl)alkyl having 1 to 3 carbons in said alkyl, phenoxyalkyl having 1 to 3 carbons in said alkyl, (substituted phenoxy)alkyl having 1 to 3 carbons in said alkyl, naphthyl and $-(CH_2)_n-Q-R°$;

wherein the substituent on said substituted phenyl, said (substituted phenyl)alkyl and said (substituted phenoxy)alkyl is selected from the group consisting of fluoro, chloro, alkyl having 1 to 3 carbons, alkoxy having 1 to 3 carbons and trifluoromethyl; n is zero, 1 or 2; Q is a divalent radical derived from a compound selected from the group consisting of furan, thiophene, pyrrole, thiazole, isothiazole, oxazole, isoxazole, 1,2,3-thiadiazole, 1,2,5-thiadiazole, tetrahydrofuran, tetrahydrothiophene, pyridine, pyrimidine, pyrazine, benzo[b]furan and benzo[b]thiophene; and R° is hydrogen or alkyl having 1 to 3 carbons;

and R[2] is selected from the group consisting of alkyl having 1 to 6 carbons, cycloalkyl having 3 to 7 carbons, phenoxymethyl, furyl, thienyl, pyridyl and

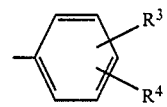

wherein R[3] and R[4] are each selected from the group consisting of hydrogen, fluoro, chloro, alkyl having 1 to 4 carbons, alkoxy having 1 to 4 carbons and trifluoromethyl.

28. The method according to claim 27, wherein X and Y are each selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons and trifluoromethyl;

or X and Y when taken together are a 4,5-, 5,6- or 6,7-methylenedioxy group or a 4,5-, 5,6- or 6,7-ethylenedioxy group;

R[1] is selected from the group consisting of alkyl having 1 to 6 carbons, cycloalkyl having 3 to 7 carbons, phenyl, phenylalkyl having 1 to 3 carbons in said alkyl, phenoxyalkyl having 1 to 3 carbons in said alkyl, furyl, thienyl, pyrrolyl, alkylfuryl having 1 to 3 carbons in said alkyl, alkylthienyl having 1 to 3 carbons in said alkyl, furylalkyl having 1 to 3 carbons in said alkyl, thienylalkyl having 1 to 3 carbons in said alkyl, naphthyl, benzo[b]furyl and benzo[b]thienyl;

and R[2] is selected from the group consisting of alkyl having 1 to 6 carbons, cycloalkyl having 3 to 7 carbons, phenoxymethyl and

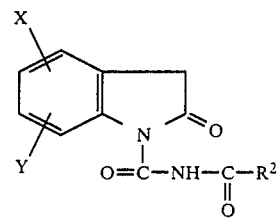

wherein R[3] and R[4] are each selected from the group consisting of hydrogen, fluoro, chloro, alkyl having 1 to 4 carbons, alkoxy having 1 to 4 carbons and trifluoromethyl.

29. The method according to claim 28, wherein X and Y are both hydrogen.

30. The method according to claim 29, wherein R[1] is selected from 2-furyl, 2-thienyl and (2-thienyl)methyl.

31. The method according to claim 30, wherein R[2] is phenyl.

32. The method according to claim 31, wherein R[1] is 2-furyl.

33. The method according to claim 28, wherein X is 5-chloro and Y is hydrogen.

34. The method according to claim 33, wherein R[1] is selected from the group consisting of 2-furyl, 2-thienyl and (2-thienyl)methyl.

35. The method according to claim 34, wherein R[2] is cyclohexyl.

36. The method according to claim 35, wherein R[1] is 2-thienyl.

37. A pharmaceutical composition useful as an analgesic and anti-inflammatory agent in a mammalian subject, which comprises a pharmaceutically-acceptable carrier and an analgesic response eliciting or inflammatory disease treating amount of a 2-oxindole compound according to claim 1, and wherein the weight ratio of the pharmaceutically-acceptable carrier to the 2-oxindole compound is in the range from 4:1 to 1:4.

38. A compound of the formula and the base salts thereof; wherein

X is selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons, trifluoromethyl, alkylsulfinyl having 1 to 4 carbons, alkylsulfonyl having 1 to 4 carbons, nitro, phenyl, alkanoyl having 2 to 4 carbons, benzoyl, thenoyl, alkanamido having 2 to 4 carbons, benzamido and N,N-dialkylsulfamoyl having 1 to 3 carbons in each of said alkyls; and Y is selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons and trifluoromethyl;

or X and Y when taken together are a 4,5-, 5,6- or 6,7-methylenedioxy group or a 4,5-, 5,6- or 6,7ethylenedioxy group;

or X and Y when taken together and when attached to adjacent carbon atoms, form a divalent radical Z, wherein Z is selected from the group consisting of

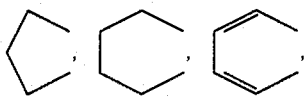

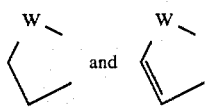 and wherein W is oxygen or sulfur;

and $R^2$ is selected from the group consisting of alkyl having 1 to 6 carbons, cycloalkyl having 3 to 7 carbons, phenoxymethyl, furyl, thienyl, pyridyl and

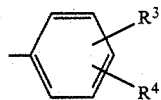

wherein $R^3$ and $R^4$ are each selected from the group consisting of hydrogen, fluoro, chloro, alkyl having 1 to 4 carbons, alkoxy having 1 to 4 carbons and trifluoromethyl.

39. A compound according to claim 38, wherein X and Y are each selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons and trifluoromethyl;

or X and Y when taken together are a 4,5-, 5,6- or 6,7-methylenedioxy group or a 4,5-, 5,6- or 6,7-ethylenedioxy group;

and $R^2$ is selected from the group consisting of alkyl having 1 to 6 carbons, cycloalkyl having 3 to 7 carbons, phenoxymethyl and

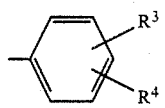

wherein $R^3$ and $R^4$ are each selected from the group consisting of hydrogen, fluoro, chloro, alkyl having 1 to 4 carbons, alkoxy having 1 to 4 carbons and trifluoromethyl.

40. A compound according to claim 39, wherein Y is hydrogen.

41. A compound according to claim 40, wherein X is hydrogen.

42. The compound according to claim 41, wherein $R^2$ is cyclohexyl.

43. The compound according to claim 41, wherein $R^2$ is phenyl.

44. A compound according to claim 40, wherein X is 5-chloro.

45. The compound according to claim 44, wherein $R^2$ is cyclohexyl.

* * * * *